US 6,545,753 B2

(12) United States Patent
Subramanian et al.

(10) Patent No.: US 6,545,753 B2
(45) Date of Patent: Apr. 8, 2003

(54) USING SCATTEROMETRY FOR ETCH END POINTS FOR DUAL DAMASCENE PROCESS

(75) Inventors: Ramkumar Subramanian, San Jose, CA (US); Bhanwar Singh, Morgan Hill, CA (US); Michael K. Templeton, Atherton, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 28 days.

(21) Appl. No.: 09/893,186

(22) Filed: Jun. 27, 2001

(65) Prior Publication Data

US 2003/0000644 A1 Jan. 2, 2003

(51) Int. Cl.$^7$ .............................................. G01N 21/00

(52) U.S. Cl. .................................................... 356/237.5

(58) Field of Search ............................... 324/323, 332, 324/337; 356/237.1, 237.2–237.5, 448; 716/4; 156/345

(56) References Cited

U.S. PATENT DOCUMENTS

| | | | | |
|---|---|---|---|---|
| 4,948,259 A | | 8/1990 | Enke et al. ................. | 356/382 |
| 5,719,495 A | | 2/1998 | Moslehi .................... | 324/158.1 |
| 5,867,276 A | | 2/1999 | McNeil et al. ............. | 356/445 |
| 5,889,593 A | * | 3/1999 | Bareket ..................... | 356/445 |
| 6,259,521 B1 | * | 7/2001 | Miller et al. .............. | 356/237.5 |
| 6,270,622 B1 | * | 8/2001 | Klippert et al. ........... | 156/345.12 |

FOREIGN PATENT DOCUMENTS

| | | | | |
|---|---|---|---|---|
| EP | 841692 A2 | 5/1998 | ........... | H01L/21/66 |
| WO | 0123871 | 4/2001 | .......... | G01N/21/95 |

OTHER PUBLICATIONS

International Search Report PCT/US 02/02990.
Derwent Abstracted Publication No. EP 756318A "Method for real–time and in situ monitoring of trench tformation process . . . " Canteloup et al. Sep. 15, 1998.*
S. Wolf and R.N. Tauber "Silicon Processing for the VLSI Era vol. 1" pp. 518 and 540–541, provided.*
Niu, X., et al., *"Specular Spectroscopic Scatterometry in DUV Lithography,"* Timbre Technology, Inc., et al.
Smith, T., et al., *"Process Control in the Semiconductor Industry,"* http://www-mtl.mit.edu/taber/Research/Process_Control/IERC99/ pp1–24.
Cote, D.R., et al., *"plasma–assisted chemical vapor deposition of dielectric thin films for ULSI semiconductor circuits,"* IBM Journal of Research & Development, vol. 43, No. 1/2 pp 1–30.

* cited by examiner

Primary Examiner—Carl Whitehead, Jr.
Assistant Examiner—Craig Thompson
(74) Attorney, Agent, or Firm—Amin & Turocy, LLP

(57) ABSTRACT

A system for monitoring and/or controlling an etch process associated with a dual damascene process via scatterometry based processing is provided. The system includes one or more light sources, each light source directing light to one or more features and/or gratings on a wafer. Light reflected from the features and/or gratings is collected by a measuring system, which processes the collected light. The collected light is indicative of the etch results achieved at respective portions of the wafer. The measuring system provides etching related data to a processor that determines the desirability of the etching of the respective portions of the wafer. The system also includes one or more etching devices, each such device corresponding to a portion of the wafer and providing for the etching thereof. The processor produces a real time feed forward information to control the etch process, in particular, terminating the etch process when desired end points have been encountered.

16 Claims, 21 Drawing Sheets

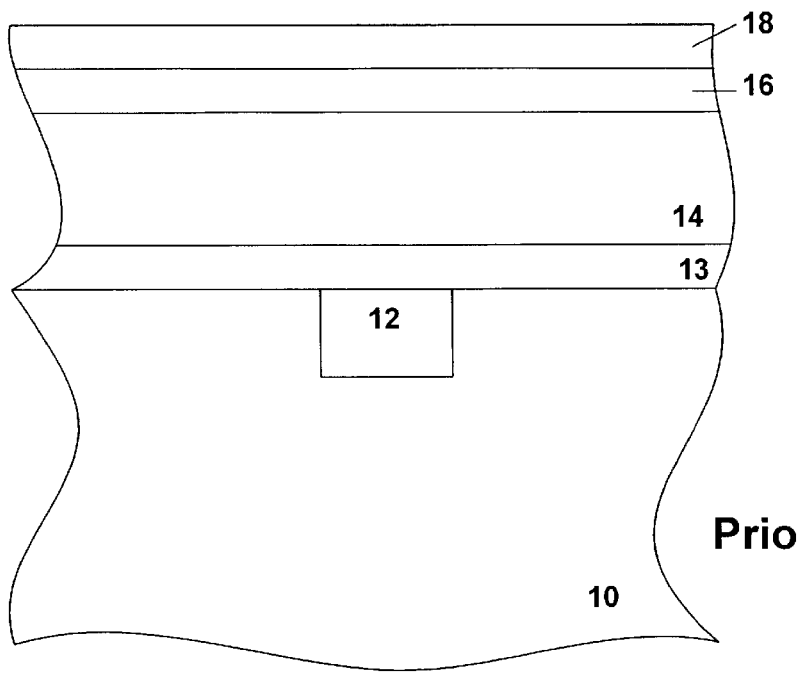
Prior Art Fig. 3
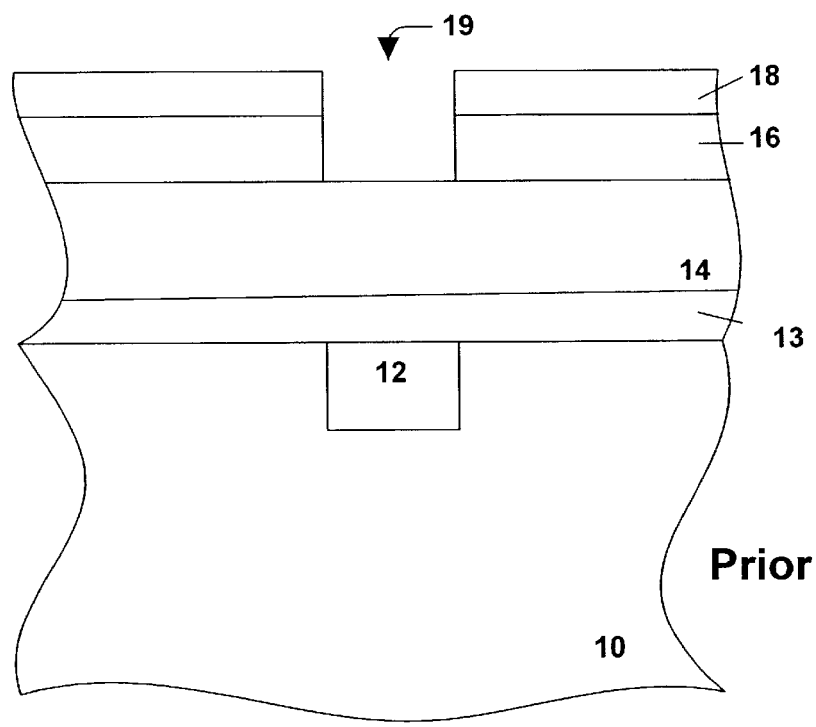
Prior Art Fig. 4

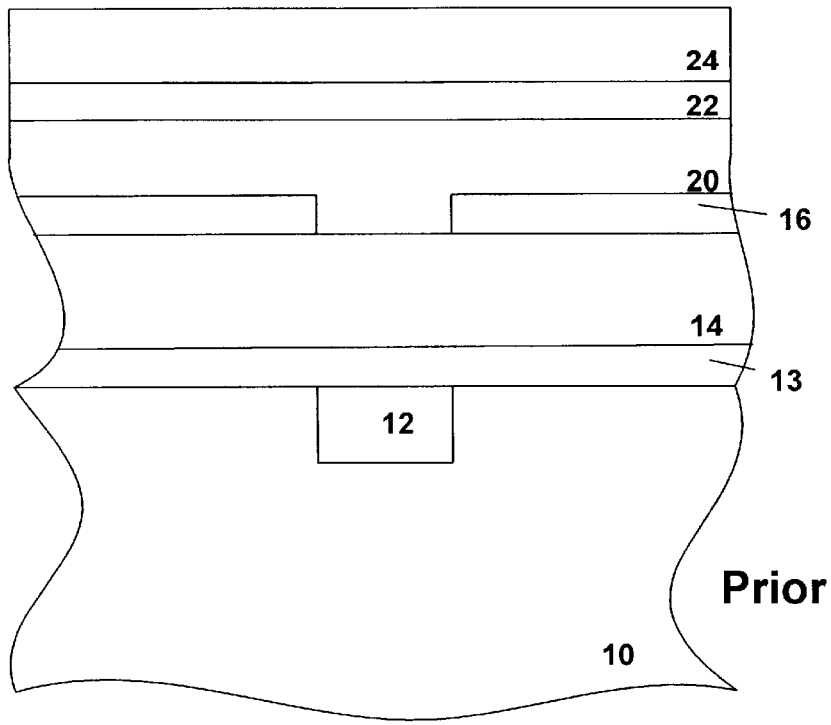
Prior Art Fig. 5
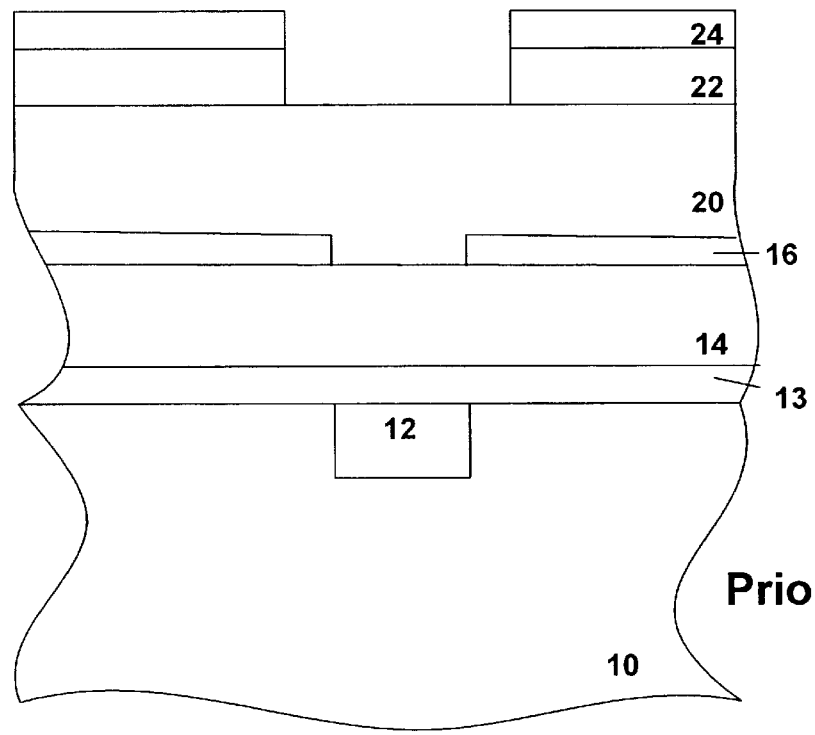
Prior Art Fig. 6

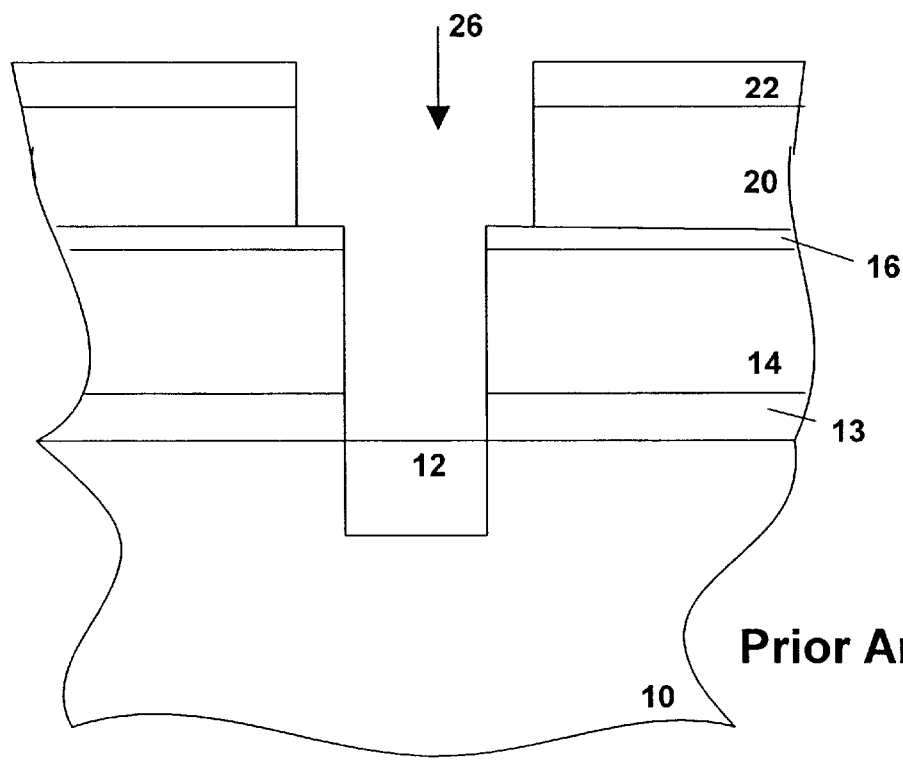
Prior Art Fig. 7
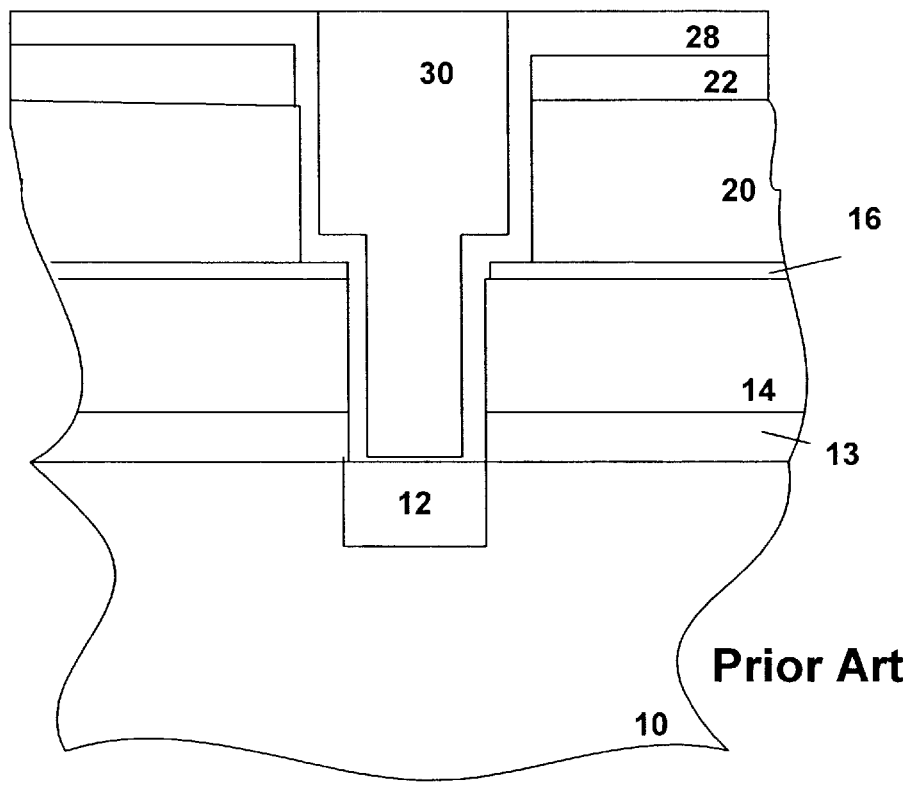
Prior Art Fig. 8

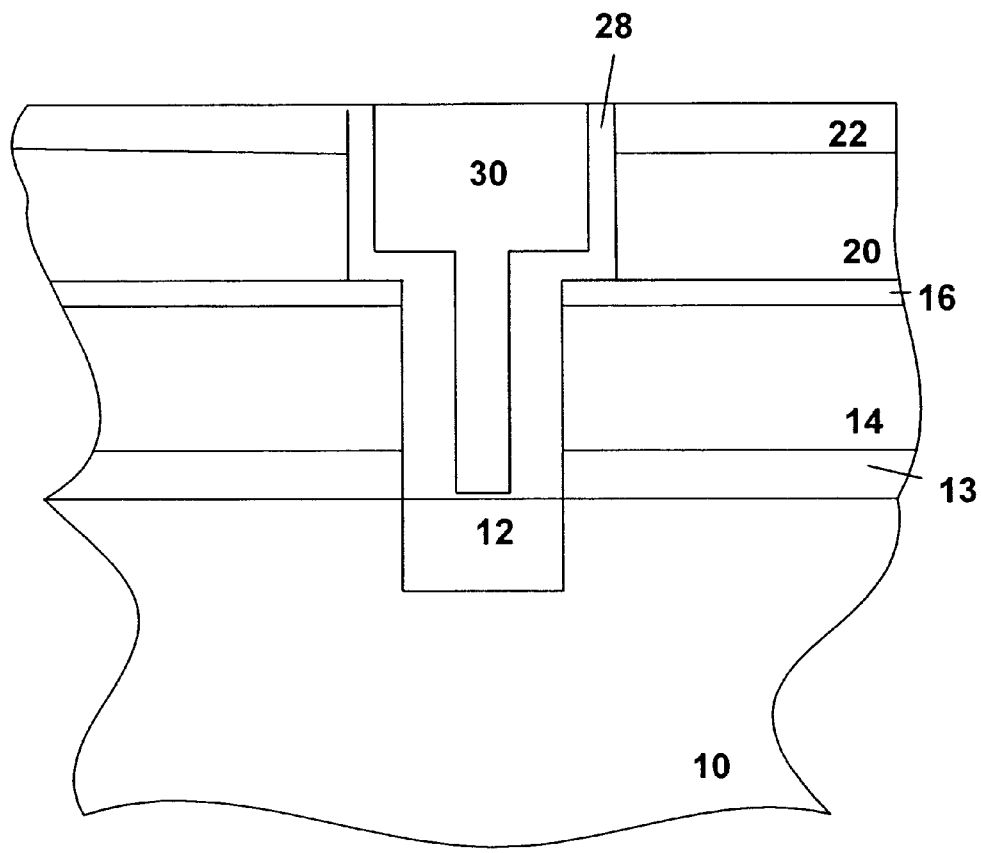
Prior Art Fig. 9

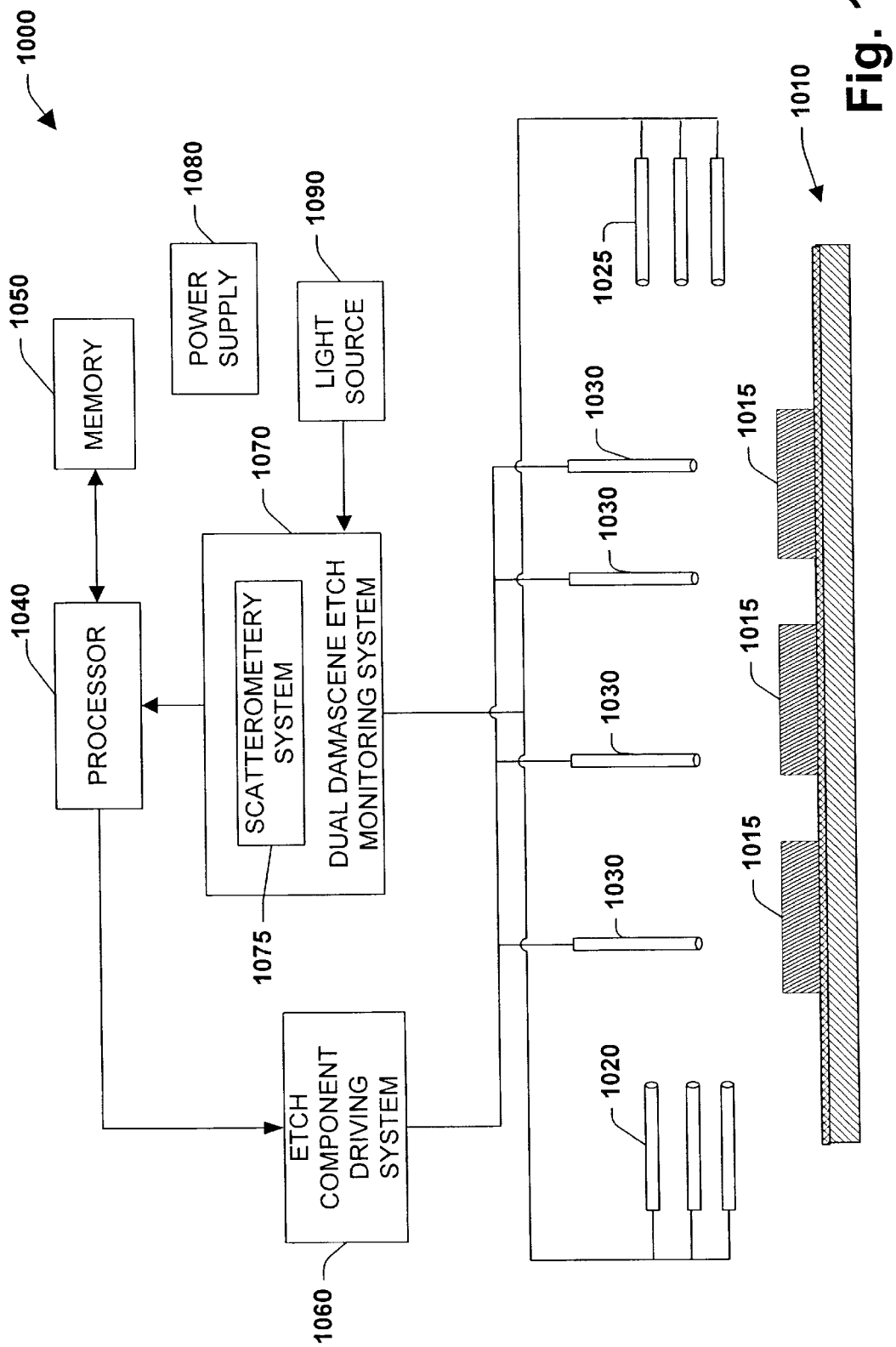

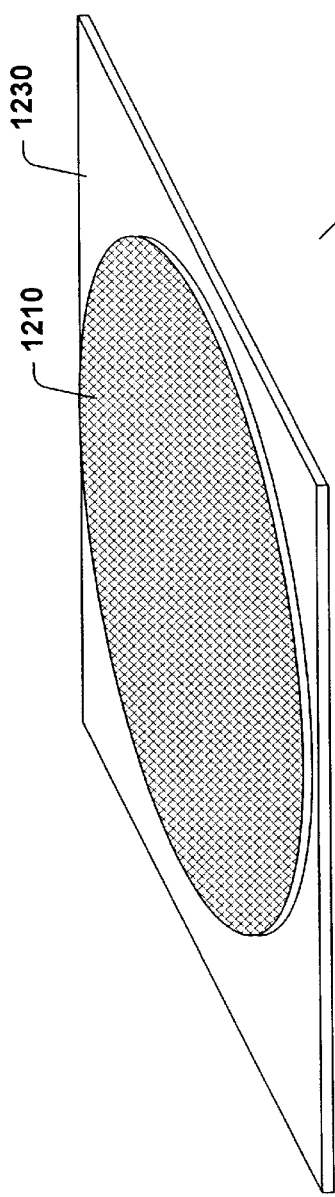
Fig. 12
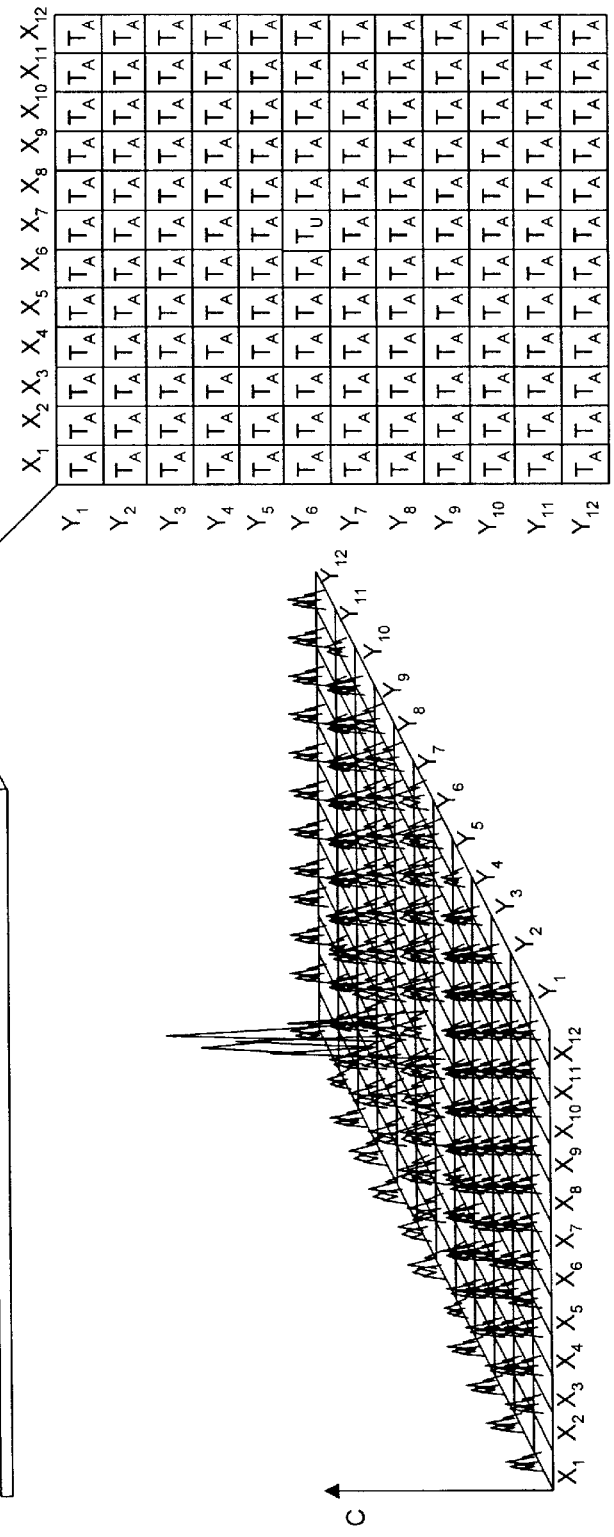
Fig. 14
Fig. 13

USING SCATTEROMETRY FOR ETCH END POINTS FOR DUAL DAMASCENE PROCESS

TECHNICAL FIELD

The present invention generally relates to a system and method for monitoring and regulating dual damascene processing of a semiconductor substrate. In particular, the present invention relates to regulating dual damascene methods of forming trenches, holes and interconnects using a dual damascene process.

BACKGROUND

In the semiconductor industry, there is a continuing trend toward higher device densities. To achieve these high densities there have been, and continue to be, efforts toward scaling down device dimensions (e.g., at sub-micron levels) on semiconductor wafers. In order to accomplish such high device packing densities, smaller and smaller feature sizes are required. This may include the width and geometry of vias between layers, the width and spacing of interconnecting lines, spacing and diameter of contact holes, and the surface geometry, such as corners and edges, of various features. The dimensions of and between such small features can be referred to as critical dimensions (CDs). Reducing CDs, and reproducing more accurate CDs facilitates achieving higher device densities.

The process of manufacturing semiconductors, or integrated circuits (commonly called ICs, or chips), typically consists of more than a hundred steps, during which hundreds of copies of an integrated circuit may be formed on a single wafer. Each step can affect the CDs of the ICs. Generally, the manufacturing process involves creating several patterned layers on and into the substrate that ultimately forms the complete integrated circuit. This layering process creates electrically active regions in and on the semiconductor wafer surface. One of the steps employed in manufacturing a semiconductor is an etch step, where selected portions of a layer (e.g., unprotected oxide layer) are removed from a wafer. Such an etch step may comprise a multi-step process that may be performed many times during the fabrication of a semiconductor. Thus, the size, shape and isolation of the electrically active regions, and thus the reliability and performance of integrated circuits employing such regions depend, at least in part, on the precision with which etching can be performed. One particular etching process is known as a dual damascene process. Conventionally, such dual damascene processes have relied on etch-stop layers and/or reproducing etch times to facilitate achieving desired etch depths for vias and/or trenches. But such conventional techniques suffer from drawbacks (e.g., additional layer, inexact/indirect control).

Conventional semiconductor devices typically comprise a semiconductor substrate, normally made of monocrystalline silicon, and a plurality of dielectric and conductive layers formed thereon. An integrated circuit is formed containing a plurality of conductive patterns comprising conductive lines separated by interwiring spacings, and a plurality of interconnect lines, such as bus lines, bit lines, word lines and logic interconnect lines. Such interconnection lines, made of metal interconnect materials, generally constitute a limiting factor in terms of size (width) and various functional characteristics of the integrated circuit. As such, there exists a need to provide a reliable interconnection structure having a small size yet capable of achieving higher operating speeds, improved signal-to-noise ratio and improved reliability.

Using a dual damascene process, semiconductor devices are patterned with several thousand openings for conductive lines and vias which are filled with a conductive metal, such as aluminum or copper, and serve to interconnect the active and/or passive elements of the integrated circuit. The dual damascene process also is used for forming the multilevel signal lines of conductive metal in the insulating layers of multilayer substrate on which semiconductor devices are mounted.

Due to the extremely fine patterns that are exposed on the photo resist, controlling the dual damascene process, whereby oxide and/or other conductive or insulating layers are removed, is a significant factor in achieving desired critical dimensions. Achieving greater precision in dual damascene processes can result, for example, in achieving more precise CDs (e.g., desired via depths). Thus, a system and/or method to control dual damascene processes is desired.

SUMMARY OF THE INVENTION

The following presents a simplified summary of the invention in order to provide a basic understanding of some aspects of the invention. This summary is not an extensive overview of the invention. It is not intended to identify key or critical elements of the invention or to delineate the scope of the invention. Its sole purpose is to present some concepts of the invention in a simplified form as a prelude to the more detailed description that is presented later.

The present invention provides a system and method for monitoring and/or controlling dual damascene methods so that an etch-stop layer is not required and so that more precise control than is possible via timed etch processes is achieved. An exemplary system can employ one or more light sources arranged to project light onto one or more features and/or gratings on a wafer, and one or more light sensing devices (e.g., photo detector, photodiode) for detecting light reflected and/or refracted by the one or more features (e.g., trenches, vias) and/or gratings as the features and/or gratings are being processed by a dual damascene method. A grating is usually divided into a large number of sufficiently thin planar grating slabs to approximate an arbitrary profile. During dual damascene processing, the light reflected from the one or more features and/or gratings is indicative of at least one parameter of the dual damascene process (e.g., depth of etch, percent completion of etching) that can be measured to determine whether desired depths, diameters, profiles, critical dimensions (CDs), and so on are being achieved and to determine whether adaptations to the dual damascene process should be undertaken.

One or more etching components can be arranged to correspond to a particular wafer portion. Alternatively, one or more etching components can be employed to etch various wafer portions. The etching components may be, for example, a gas plasma apparatus employed in reactive ion etching. It is to be appreciated that any suitable etching components may be employed with the present invention. The etching components are selectively driven by the system to etch away oxide and/or other materials (e.g., in a polysilicon) at a desired location, at a desired rate, to a desired depth and/or to a desired width. The etching process is monitored by the system by comparing the etch results (e.g., CDs, depth, height, profiles) on the features and/or gratings on the wafer to desired results. Data gathered during such monitoring can be employed to determine whether an etch process employed in a dual damascene method is complete, and thus, to control the end point of such a dual damascene etch process. As a result, more optimal etching process characterization is achieved, which can reduce the time and expense of producing an etch process that can subsequently be employed to produce high quality integrated circuits. Additionally, and/or alternatively, data concerning etch process conditions that resulted in favorable and/or unfavorable CDs can be stored to facilitate reproducing favorable etch process conditions for subsequent portions of the wafer being etched and/or for subsequent wafers. In one example of the present invention, the data that is gathered is analyzed using machine learning techniques to facilitate more quickly and more accurately adapting the etch process being characterized and to facilitate more quickly and more accurately adapting subsequent etch processes.

One aspect of the present invention provides a system for monitoring and controlling an etch process associated with a dual damascene process. The system includes an etching component operative to etch a portion of a wafer and an etch component driving system operably connected to the etching component, where the etch component driving system is adapted to drive the at least one etching component. The system also includes a system for directing light towards gratings and/or features located on a portion of the wafer and an etch monitoring system operable to measure etching results from light reflected from the gratings and/or features. The system also includes a processor operatively coupled to the etching monitoring system and the etch component driving system, where the processor receives an etching result data from the measuring system and analyzes the etching result data by comparing the etching result data to stored etching result data. In one example of the present invention, the system also includes a scatterometry system for processing the light reflected from the one or more gratings.

Another aspect of the present invention provides a method for monitoring and controlling an etch process associated with a dual damascene process. The method includes logically partitioning a wafer into portions, fabricating gratings to be etched on the wafer and etching the wafer. Before, during and/or after the wafer is etched, the method includes directing an incident light onto the gratings, collecting a reflected light reflected from the gratings, and analyzing the reflected light to determine etching results associated with the grating. In one example of the present invention, the method includes processing the reflected light in a scatterometry system.

To the accomplishment of the foregoing and related ends, certain illustrative aspects of the invention are described herein in connection with the following description and the annexed drawings. These aspects are indicative, however, of but a few of the various ways in which the principles of the invention may be employed and the present invention is intended to include all such aspects and their equivalents. Other advantages and novel features of the invention may become apparent from the following detailed description of the invention when considered in conjunction with the drawings.

BRIEF DESCRIPTION OF THE DRAWINGS

Prior Art FIG. 3 illustrates a cross-sectional view of a semiconductor substrate having a low k material layer and a photoresist layer.

Figure Art FIG. 4 illustrates a cross-sectional view of the semiconductor substrate of Prior Art FIG. 3 after patterning of certain layers.

Prior Art FIG. 5 illustrates a cross-sectional view of the semiconductor substrate of Prior Art FIG. 4 after another low k material layer is formed.

Prior Art FIG. 6 illustrates a cross-sectional view of the semiconductor substrate of Prior Art FIG. 5 after patterning of certain layers.

Prior Art FIG. 7 illustrates a cross-sectional view of the semiconductor substrate of Prior Art FIG. 6 after a portion of the low k material is removed.

Prior Art FIG. 8 illustrates a cross-sectional view of the semiconductor substrate of Prior Art FIG. 7 after a barrier layer and a conductive layer are formed.

Prior Art FIG. 9 illustrates a cross-sectional view of the semiconductor substrate of Prior Art FIG. 8 after the substrate is planarized.

FIG. 10 is schematic block diagram of a dual damascene monitoring and controlling system in accordance with an aspect of the present invention.

FIG. 12 is a perspective illustration of a wafer that may be monitored in accordance with an aspect of the present invention.

FIG. 13 is a representative three-dimensional grid map of a wafer illustrating measurements taken in accordance with an aspect of the present invention.

FIG. 14 is a measurement table correlating the measurements of FIG. 13 with stored measurements in accordance with the present invention.

DETAILED DESCRIPTION OF THE INVENTION

Figure 1:
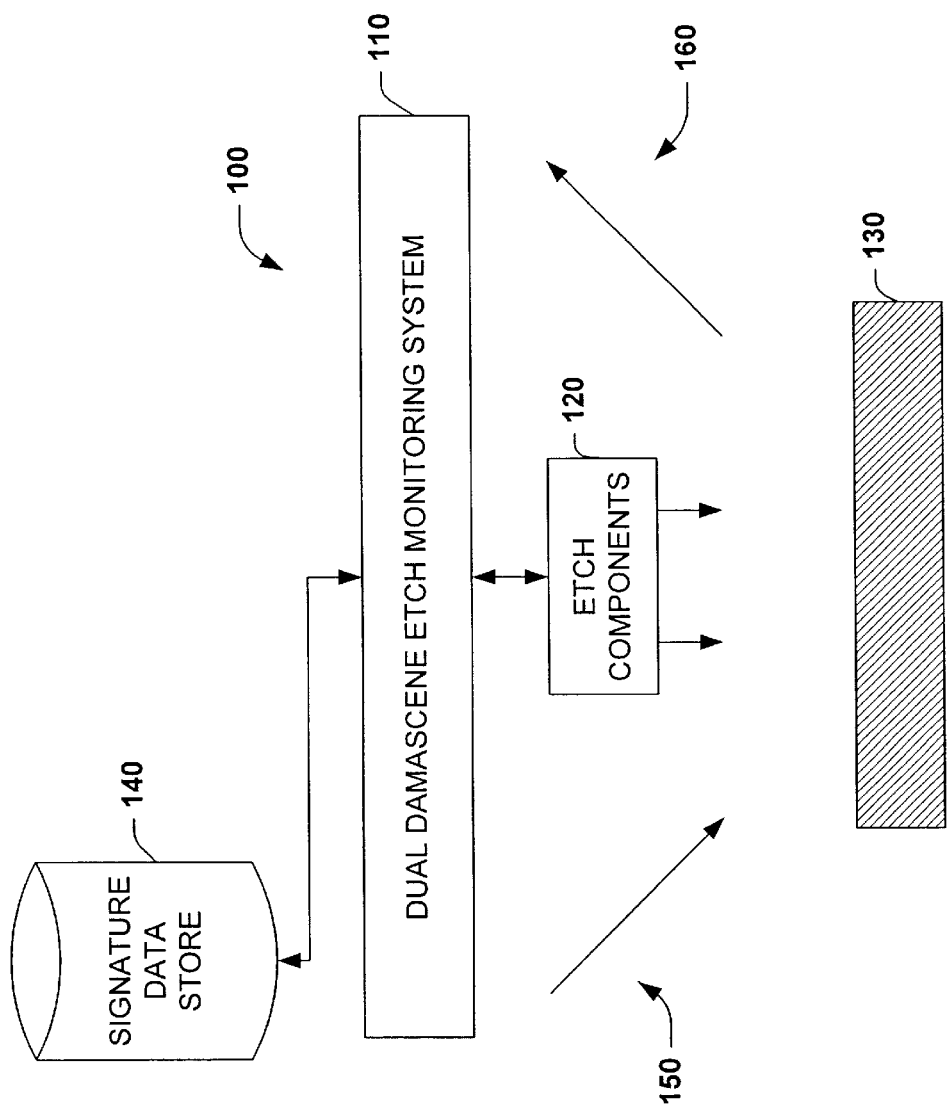
FIG. 1 is a schematic block diagram of a system for monitoring and/or controlling an etch process involved in dual damascene processing in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, to one skilled in the art that the present invention may be practiced without these specific details. In other instances, well-known structures and devices are shown in block diagram form in order to facilitate describing the present invention.

The term "component" refers to a computer-related entity, either hardware, a combination of hardware and software, software, or software in execution. For example, a component may be a process running on a processor, a processor, an object, an executable, a thread of execution, a program and a computer. By way of illustration, both an application running on a server and the server can be components. By way of further illustration, both an ion gun and a process controlling an ion gun can be components.

It is to be appreciated that various aspects of the present invention may employ technologies associated with facilitating unconstrained optimization and/or minimization of error costs. Thus, non-linear training systems/methodologies (e.g., back propagation, Bayesian, fuzzy sets, non-linear regression, or other neural networking paradigms including mixture of experts, cerebella model arithmetic computer (CMACS), radial basis functions, directed search networks and function link networks) may be employed.

Referring initially to FIG. 1, a system 100 for monitoring a dual damascene process is illustrated. Such processes may be employed, for example, to create vias in an integrated circuit. While the illustrations associated with this application primarily depict etching occurring directly under one or more etch components, it is to be appreciated that directional etches may also be employed by the present invention. In plasma etching systems, specific gases are fed into a reaction chamber. There, the plasma creates reactive species from those gases. The etch rate is generally proportional to the concentration of the reactive species. Thus, conventional techniques may employ indirect measurements, including analyzing the reacted gases, to determine etching progress. But such techniques do not provide direct information concerning etch results (e.g., CDs, depths, profiles) being achieved on a wafer 130.

The system 100 includes an dual damascene etch monitoring system 110 operative to direct a light 150 at a wafer 130 that is going to be etched or that is in the process of being etched. The dual damascene etch monitoring system 110 can be a standalone device and/or can also be distributed between two or more cooperating devices and/or processes. The dual damascene etch monitoring system 110 can reside in one physical or logical device (e.g., computer, process) and/or be distributed between two or more physical or logical devices. The dual damascene etch monitoring system 110 may include one or more components that are located inside a process chamber and/or one or more components that are not located inside a process chamber. The etch components 120 may be employed, for example, in dry-etching techniques where the mechanism of etching has a physical basis (e.g., glow-discharge sputtering, ion-milling), a chemical basis (e.g., plasma etching), and a combination of bases (e.g., reactive ion etching (RIE), ion-enhanced etching). The etch components 120 may be operatively connected to the dual damascene etch monitoring system 110 to supply data concerning current operating characteristics (e.g., temperature, pressure, formula).

The light 150 may be generated by many different light sources, and in one example aspect of the present invention the light 150 is generated by a frequency-stabilized laser. The dual damascene etch monitoring system 110 may direct the light 150 at substantially all of the wafer 130 and/or at selected portions of the wafer. By way of illustration, in one example aspect of the present invention, the light 150 may be directed at selected portions of the wafer 130, where such portions provide data sufficient to generate scatterometry signatures. A light 160 reflected from the wafer 130 is collected by the dual damascene etch monitoring system 110, which may then employ scatterometry techniques to analyze the reflected light 160 to determine one or more etch results achieved on the wafer 130. For example, the depth of trenches and/or interconnecting holes may be analyzed. Other parameters including, but not limited to horizontal etch rate, vertical etch rate, etch-rate percent uniformity and isotropic versus anisotropic effects may also be analyzed.

It is to be appreciated that the surface of the wafer 130, including features, can both reflect and refract the light 150, so that the light 160 can be a complex reflected and/or refracted light. The scatterometry analysis can include comparing one or more scatterometry signatures associated with the reflected light 160 to one or more scatterometry signatures stored in a signature data store 140. Such signatures may be generated, for example, by combining phase and intensity information associated with the reflected light 160. As etching progresses, light reflecting from a wafer 130 may produce various signatures. The sequence in which such signatures are generated can be employed to determine the rate at which etching is progressing, which can in turn be employed to characterize the etch process. For example, at a first point in time T1, light reflected from the wafer 130 may produce a signature S1 that indicates that a trench of a first depth D1 have been produced. Similarly, at a second point in time T2, light reflected from the wafer 130 may produce a signature S2 that indicates that trenches with a second depth D2 have been produced and at a third point in time T3, light reflected from the wafer 130 may produce a signature S3 that indicates that trenches with a third depth D3 have been produced. Analyzing the signatures can facilitate determining when a desired depth has been achieved, thus removing the need for an etch-stop layer and/or timed etch processes, providing advantages over conventional systems. Analyzing the sequence of signatures, and the time required to produce transitions between such signatures can facilitate determining whether etching is progressing at an acceptable rate.

The signature data store 140 can store data in data structures including, but not limited to one or more lists, arrays, tables, databases, stacks, heaps, linked lists and data cubes. The signature data store 140 can reside on one physical device and/or may be distributed between two or more physical devices (e.g., disk drives, tape drives, memory units). Analyses associated with the reflected light 160 and/or the signatures stored in the signature data store 140 can be employed to control one or more etching components 120. For example, analyses associated with the reflected light 160 can be employed to terminate the processing of the etching components 120. It is to be appreciated that the etching components 120 can include, but are not limited to, isotropic and/or anisotropic etching components. It is to be further appreciated that the etching components 120 can be employed to remove exposed regions of a positive photoresist mask and/or unexposed regions of a negative photoresist mask using techniques like reactive ion etching, for example.

The precision with which resist portions are removed to create vias and interconnecting holes and the resulting precision in the distance between the remaining portions corresponds to the precision with which desired profiles, depths, CDs, etc. are achieved. Therefore, the precision of the processing performed by the etch components 120 is directly related to the feature sizes and CDs that can be achieved on the wafer 130. Gathering real time etch process data facilitates determining the effect of controlling the etch components 120 and thus facilitates more quickly and more accurately determining desired etch component 120 adaptations that will result in higher quality ICs.

Figure 2:
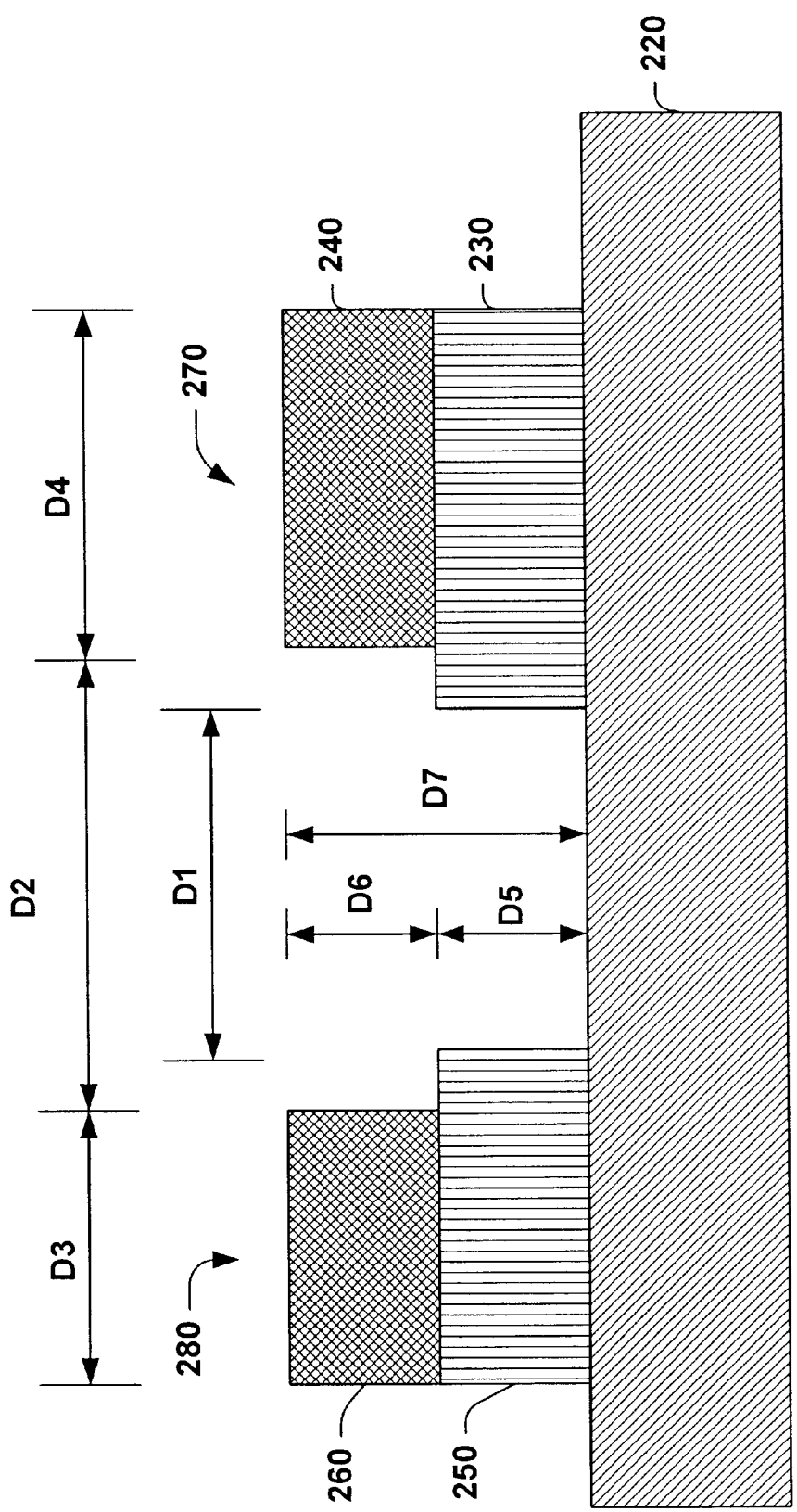
FIG. 2 is a cross-sectional view of CD measurements that may be monitored in accordance with an aspect of the present invention.

Turning now to FIG. 2, measurements that may affect signatures generated by a scatterometry system associated with monitoring and/or controlling a dual damascene process are illustrated. Controlling such measurements (e.g., width, depth, diameter, thickness) can be important to reliable and efficient operation of an integrated circuit.

A wafer 220 is illustrated with two features 270 and 280, between which there is a gap. The gap may have a depth of distance D7, where the depth D7 includes the depth D5 and the depth D6. Conventionally, controlling the depths D5 and/or D6, and thus the depth D7, may have required an etch-stop layer, to prevent the depth D7 from becoming too large. But including an etch-stop layer complicates, and thus makes more expensive, the fabrication of integrated circuits employing such etch-stop layers. Also conventionally, controlling the depths D5 and/or D6, and thus the depth D7 may have relied on pre-computed etch times. But such pre-computed etch times rely on indirect observation and do not account for wafer-to-wafer and/or feature-to-feature variations. Thus, the present invention employs scatterometry techniques to monitor the depths D5, D6 and D7, and to control the etch process(es) employed to create gaps with such depths.

While the depths D5, D6 and D7 are being monitored and controlled, horizontal distances may also be monitored, with such monitoring contributing to the control of the dual damascene process. Thus, the wafer 220 is illustrated with two features 270 and 280. The feature 270 is illustrated with an oxide layer 230 and a hardened photoresist layer 240. Similarly, the feature 280 is illustrated with an oxide layer 250 and a hardened photoresist layer 260. While the oxide layers 250 and 230 are separated by a distance D1, this distance may, for example, be too small for reliable operation of the integrated circuit being fabricated on the wafer 220. A desired critical dimension for the distance between the oxide layer 250 and the oxide layer 230 may be the distance D2. For example, a gap of size D2 may be required to facilitate fabricating a connecting line. Lithography sufficient to harden the photoresist layer 260 and the photoresist layer 270 may have been achieved in earlier fabrication steps, but such precise lithography may go to waste if precise etching of the features 270 and 280 can not be achieved. For example, sophisticated lithography may have produced the hardened photoresist 260 with a desired width of D3. Similarly, sophisticated lithography may have produced the hardened photoresist layer 240 with a desired width of D4, which should suffice to facilitate etching the oxide layers 250 and 230 if precise etching control is possible. But if precise etching control is not possible, then the distance D1 may be maintained, and reliable operation may not be achieved and/or the connecting line may not be able to be created.

Thus, the present invention facilitates generating information concerning measurements (e.g., the distances D1, D2, D3, D4, D5, D6 and D7) and the resulting topographies of layers. Scatterometry-based real time control of the features 270 and 280, and thus the gap between the features 270 and 280, which may be employed for an interconnecting line, can be employed to control an etch process associated with a dual damascene process, and to determine the desirability of adaptations to one or more etch parameters (e.g., temperature, formula, angle, direction, pressure). Such information, generated, at least in part, in response to in situ reflected light being analyzed by scatterometry techniques can be employed to generate process history data that can be employed to adapt future etch processes that are characterized by machine learning techniques that have access to such history data, thus providing advantages over conventional systems. For example, one or more signatures associated with the wafer 220 and/or the features 270 and 280 can be generated. At a first point in time T10, a signature S10 may be generated that indicates that desired critical dimensions have not been achieved. Thus, an etching process may be adapted in an attempt to achieve the desired critical dimension. Then, at a second point in time T11, a signature S11 may be generated that indicates that although the desired critical dimensions have still not been achieved, that progress toward the desired critical dimensions have occurred. The etching process may then be continued until a later point in time T12, when a signature S12 indicates that the desired critical dimensions have been achieved. But the signature S11 may have indicated that the adaptation to the etching process produced a movement away from desired critical dimensions, and thus the etch process may have been terminated, and the wafer marked for discard, for example.

Prior Art FIGS. 3–9 illustrate one conventional method of dual damascene processing that employs an etch-stop layer. The present invention facilitates performing an analogous dual damascene process (illustrated in FIGS. 23–29) where the etch-stop layer is not required due to etch monitoring and controlling provided by a scatterometry based system. With regard to the description of the embodiment of Prior Art FIGS. 3–9, the term substrate includes not only a semiconductor substrate, such as semiconductor substrate 10, but also any and all layers and structures fabricated over the semiconductor substrate up to the point of processing under discussion.

Prior Art FIGS. 3–9 illustrate a method in connection with forming interconnections that make electrical contact to a metal structure 12 within a semiconductor substrate 10, where the method includes an etch-stop layer 13. However, the method of Prior Art FIGS. 3–9 may be used to form interconnects for other purposes. For example, the method of Prior Art FIGS. 3–9 may be adapted to making electrical contacts to various device structures, active elements and passive elements including polysilicon gates, wordlines, source regions, drain regions, bit lines, bases, emitters, collectors, conductive lines, conductive plugs, diffusion regions, etc. The method of Prior Art FIGS. 3–9 may be used with any suitable semiconductor technology including but not limited to NMOS, PMOS, CMOS, BiCMOS, bipolar, multi-chip modules (MCM) and III–IV semiconductors.

Referring to Prior Art FIG. 3, a semiconductor substrate 10 having a metal structure 12 is provided. Semiconductor substrate 10 may include any suitable semiconductor material, for example, a monocrystalline silicon substrate. Metal structure 12 may be any structure to which an electrical contact is desired, for example, a copper line. An insulation material layer 13, such as silicon nitride, is formed over the substrate 10. The insulation material layer 13 may act as an etch-stop layer. The present invention facilitates mitigating problems that the etch-stop layer is designed to mitigate, and thus, the present invention facilitates performing a dual damascene process without the etch-stop layer 13. The insulation material layer 13 may include one or more of silicon dioxide, silicon oxynitride, boronitride, silicon boronitride and silicon carbide, for example. The insulation material layer 13 may be formed to any suitable thickness using any suitable technique, for instance, using chemical vapor deposition (CVD) techniques. CVD techniques include low pressure chemical vapor deposition (LPCVD) or plasma enhanced chemical vapor deposition (PECVD). In one embodiment, the thickness of the insulation material layer 13 may range, for example, from about 500 Å to about 2,500 Å. The insulation material layer 13 subsequently serves as an etch stop layer for the later described low K material layers, as well as a barrier layer for the metal structure 12. A low k material layer 14, such as BCB, is formed over the insulation material 13. The low k material layer 14 may alternatively include one or more of polyimides, fluorinated polyimides, polysilsequioxane, parlene F, parlene N, amorphous polytetrafluoroethylene and Flare™ from AlliedSignal, for example. Low k material layer 14 may be formed to any suitable thickness using any suitable technique that may depend, for instance, on the material or materials used. In the case of BCB, a spin on technique is useful. Also in the case of BCB, the thickness of the low k material layer 14 may range, for example, from about 5,000 Å to about 10,000 Å.

It is to be appreciated that although Prior Art FIGS. 3–9 describe a wafer with several specific layers, that the dual damascene process described in Prior Art FIGS. 3–9 may be employed with other combinations of layers, and thus, the present invention is not limited to layer configurations described in connection with Prior Art FIGS. 3–9.

A hard mask layer 16, such as a layer of silicon dioxide, is deposited over the low k material layer 14 using suitable techniques, such as CVD techniques. The hard mask layer 16 may alternatively include one or more of silicon nitride, silicon oxynitride, boronitride, silicon boronitride and silicon carbide. The thickness of the hard mask layer 16 may range, for example, from about 500 Å to about 2,500 Å.

An ultra-thin photoresist layer 18 is deposited over the hard mask layer 16. The thickness of the ultra-thin photoresist layer 18 may range, for example, from about 500 Å to about 1,500 Å. In this embodiment, the thickness of the ultra-thin photoresist layer 18 is about 1,000 Å.

Referring to Prior Art FIG. 4, the ultra-thin photoresist layer 18 and hard mask layer 16 are patterned to define a preliminary contact opening 19 over at least a portion of a device structure, active element or passive element, or the metal structure 12 in this instance. Any suitable patterning technique may be used to define the preliminary contact opening 19 in the ultra-thin photoresist layer 18 and hard mask layer 16. For example, standard photolithographic techniques may be used. In particular, the ultra-thin photoresist layer 18 is exposed to radiation and developed to provide a patterned photoresist. The patterned photoresist is formed using electromagnetic radiation having a relatively small wavelength (for example, less than 365 nm). In this embodiment, electromagnetic radiation having a wavelength of about 11 nm is employed. Either the exposed or unexposed portions of the ultra-thin photoresist layer 18 are removed or developed to provide the patterned photoresist exposing a corresponding portion of the hard mask layer 16 in preliminary contact opening 19.

The exposed portions of the hard mask layer 16 are etched anisotropically to further form preliminary contact opening 16 exposing at least a portion of the low k material layer 14. The patterned ultra-thin photoresist layer 18 may then be stripped from the substrate, and the substrate may be optionally cleaned to remove residue from preliminary contact opening 19. Since the ultra-thin photoresist layer 18 has a thickness about 2,000 Å or less, the stripping process does not materially effect the conformation of the low k material layer 14 or the preliminary contact opening 19.

Preliminary contact opening 19 may be formed to have any desired cross-section, width or diameter, such as about 0.1 μm or less, including about 0.09 μm or less, about 0.075 μm or less and about 0.05 μm or less, primarily depending upon the wavelength of radiation employed. The preliminary contact openings 19 serve to define subsequently formed contact holes. Conventionally, controlling such cross-section, width and/or diameter may involve indirect monitoring and/or control (e.g., timed etches, analyzing reacted gasses, etc.), which do not provide as precise a control as is possible with the scatterometry based system described herein.

Referring to Prior Art FIG. 5, a second low k material layer 20 may be formed to any suitable thickness using any suitable technique over the substrate, including over the hard mask layer 16 and the exposed portion of the low k material layer 14 in the preliminary contact opening 19. In this embodiment, another BCB layer is formed by spin on techniques. Also in this embodiment, the thickness of the second low k material layer 20 may range, for example, from about 5,000 Å to about 10,000 Å.

A second hard mask layer 22, such as a layer of silicon dioxide, is deposited over the second low k material layer 20 using suitable techniques, such as CVD techniques. The second hard mask layer 22 may alternatively include one or more of silicon nitride, silicon oxynitride, boronitride, silicon boronitride and silicon carbide. The thickness of the second hard mask layer 22 may range, for example, from about 500 Å to about 2,500 Å. In this embodiment, the thickness of the second hard mask layer 22 is about 1,000 Å.

A second ultra-thin photoresist layer 24 is deposited over the second hard mask layer 22. The thickness of the second ultra-thin photoresist layer 24 may range, for example, from about 500 Å to about 1,500 Å. The second ultra-thin photoresist layer 24 and the second hard mask layer 22 subsequently serve as a trench mask for forming a trench over a plurality of contact holes.

Referring to Prior Art FIG. 6, the second ultra-thin photoresist layer 24 and second hard mask layer 22 are patterned to define a trench mask over at least a portion of a device structure, active element or passive element, or the metal structure 12 in this instance. Any suitable patterning technique may be used to define the trench mask in the second ultra-thin photoresist layer 24 and second hard mask layer 22. For example, standard photolithographic techniques may be used. In particular, the second ultra-thin photoresist layer 24 is exposed to radiation and developed to provide a patterned photoresist. The patterned photoresist is formed using electromagnetic radiation having a relatively small wavelength (for example, less than 365 nm). Either the exposed or unexposed portions of the second ultra-thin photoresist layer 24 are removed or developed to provide the patterned photoresist exposing a corresponding portion of the second hard mask layer 22 in the trench region.

The exposed portions of the second hard mask layer 22 are etched anisotropically to further form the trench exposing at least a portion of the second low k material layer 20. Conventionally, controlling such etching may include employing timed etches and/or analyzing reacted gasses. Such indirect methods do not provide as precise a control as the scatterometry based system described herein. The trench may be formed to have any desired cross-section, width or diameter, such as about 0.25 $\mu$m, about 0.18 $\mu$m, about 0.15 $\mu$m, about 0.13, about 0.1 $\mu$m, about 0.075 and/or about 0.05 $\mu$m. The width of the trench may depend on the resistivity of the conductive material used for creating an interconnect within the trench. The width of the trench is typically larger than the width of previously described preliminary contact opening 19.

Referring to Prior Art FIG. 7, exposed portions of the second low k material layer 20, low k material layer 14 and insulation material layer 13 are removed in any suitable manner to define an opening 26 comprised of a trench or interconnect channel over at least one contact hole formed over metal structure 12. Any suitable etch technique may be used to etch second low k material layer 20, low k material layer 14 and insulation material layer 13. Preferably, a selective etch technique may be used to etch the material of low k material layers 20 and 14 and at a relatively greater rate as compared to the rate that the material of the insulation material layer 13, second ultra-thin photoresist layer 24, and/or second hard mask layer 22 are etched. In other words, the insulation material layer 13 serves as an etch-stop layer when etching low k material layers 20 and 14. Including such an etch-stop layer increases the complexity, and thus the cost, of the wafer upon which the integrated circuit is formed. Portions of the low k material layer 14 and second low k material layer 20 are typically etched in an anisotropic manner using an oxygen containing gas exposing a portion of the insulation material layer 13.

The exposed portion of the insulation material layer 13 is etched in an anisotropic manner using a suitable gas mixture, primarily depending upon the composition of the insulation material layer 13 exposing at least a portion of the metal structure 12. The second ultra-thin photoresist layer 24 may then be stripped from the substrate, and the substrate may be optionally cleaned to remove residue from the opening 26. However, since the second ultra-thin photoresist layer 24 has a thickness about 2,000 Å or less, the second ultra-thin photoresist layer 24 is typically removed during removal of portions of the low k material layers 14 and 20 where an oxygen containing gas is used as an etchant. In a preferred embodiment, therefore, the insulation material layer 13 and the second hard mask layer 22 contain different materials to afford etch selectivity.

Referring to Prior Art FIG. 8, a suitable conductive material or materials is formed or deposited over the substrate, including filling the opening 26 and over the second hard mask layer 22. For example, an optional barrier layer 28 and a conductive layer 30 are deposited over the substrate. The optional barrier layer 28 may serve as a diffusion barrier preventing materials from the conductive layer 30 from diffusing into the low k material layer 14 and/or second low k material layer 20. The optional barrier layer 28 is formed over the substrate so that it covers the side walls and bottom in the opening 26. The barrier layer 28 may be formed using any suitable technique to a thickness sufficient to serve as a diffusion barrier for conductive layer 30. For example, the thickness of the barrier layer 28 may be in the range from about 300 Å to about 500 Å. The barrier layer 28 is a conductive layer containing, for example, tantalum, tungsten, titanium, alloys, silicides, and/or nitrides thereof.

Referring to Prior Art FIG. 9, conductive layer 30 is planarized to the surface of the barrier layer 28; that is, portions of the conductive layer 30 are removed from the top surface of barrier layer 28 above the second hard mask layer 22. Opening 26 remains substantially filled with the barrier layer 28 and conductive layer 30. Any suitable technique may be used to planarize the substrate and may depend, for instance, on the specific identity of the material used to make the conductive layer 30. In one embodiment, the substrate is planarized (a portion of the conductive layer is removed) using chemical mechanical polishing (CMP) techniques using a polishing solution or slurry depending upon the specific identity of the materials used for the conductive layer 30. As a result of CMP techniques, dishing may occur wherein the conductive layer 30 is removed to a level below the top surface of the barrier layer 28, and in some instances, to a level just below the top surface of the second hard mask layer 22.

The portion of the optional barrier layer 28, if employed, exposed over the second hard mask layer 22 is removed using CMP techniques or an etch gas mixture. After the portion of the barrier layer exposed over the second hard mask layer 22 is removed, the substrate may be cleaned using conventional techniques such as wet cleaning techniques. Removal of the exposed portion of the barrier layer serves to planarize the substrate while leaving undisturbed the portion of the barrier layer 28 surrounding conductive layer 30. If employed, the etch gas mixture has high etch selectivity for the barrier metal as compared to a hard mask material, such as silicon oxide, which may constitute the second hard mask layer 22 as well as other conductive metals such as copper or copper alloys, which may constitute the conductive layer 30. In this embodiment, the etch gas mixture provides a selective etch such that the conductive layer 30 serves as a mask in etching the barrier layer 28. The etch gas mixture etches in an isotropic manner whereby there is no or very little change in side wall profile of the conductive layer 30.

It is to be appreciated that Prior Art FIGS. 3–9 illustrate but one example dual damascene process, and that the present invention is not limited to improving the illustrated dual damascene process, but that the present invention can be employed to improve other dual damascene processes.

FIG. 10 illustrates a system 1000 for monitoring and/or controlling an etch process involved in dual damascene processing. The system 1000 operates to monitor one or more etch components 1030 and a wafer 1010 whereupon one or more features (e.g., vias, interconnects) and/or gratings 1015 are formed. A dual damascene etch monitoring system 1070, a processor 1040 and an etch component driving system 1060 work cooperatively to control the etch components 1030 and to provide feedback information concerning the geometry (e.g., depth, diameter, profile) of the features and/or gratings 1015 and the corresponding etch component 1030 operating parameters (e.g., temperature, formula, angle, direction, pressure).

The etch components 1030 are coupled to and controlled directly by the etch component driving system 1060. The etch component driving system 1060 receives information and/or instructional commands from the processor 1040. The processor 1040 determines the content and type of information transmitted to the etch component driving system 1060 according to its analysis of data received from and collected by the dual damascene etch monitoring system 1070. Thus, through the interaction of components 1030, 1070, 1040 and 1060, the system 1000 has the ability to control the etching of the wafer 1010. In addition, by communicating measurements relating to recently etched features/wafers to the processor 1040, the processor 1040 can control the etching component driving system 1060, which can thus regulate the one or more etching components 1030 to facilitate obtaining more precise and improved etching processes. Thus etching errors can be mitigated and higher packing densities and smaller feature sizes can be achieved. Furthermore, rather than relying on timed etch processes and/or an etch-stop layer in a dual damascene process, the etching components 1030 can be controlled to etch until a desired depth in one or more trenches and/or vias is achieved and then to stop etching. Thus, more precise depth control can be achieved, and the need for timed etching and/or etch-stop layers is mitigated.

The system 1000 includes one or more etching components 1030 that are selectively controlled to facilitate controlled etching of the wafer 1010. One or more target light sources 1020 project light onto respective portions of the wafer 1010. A portion of the wafer 1010 may have one or more gratings 1015 and/or features located on that portion. Light reflected and/or refracted by the one or more gratings 1015 is collected by one or more light detecting components 1025, and processed by a dual damascene etch monitoring system 1070 to measure at least one parameter relating to the etching of one or more features and/or the one or more gratings 1015. By way of illustration and not limitation, the depth and/or geometry of a trench and/or hole for an interconnecting line can be measured. By way of further illustration, spaces between portions of the grating 1015 and spaces between the gratings 1015 can be measured and compared to desired critical dimensions (CDs). The reflected light is measured with respect to the incident light in order to obtain the various parameters relating to the gratings 1015.

The dual damascene etch monitoring system 1070 includes a scatterometry system 1075. It is to be appreciated that any suitable scatterometry system may be employed to carry out the present invention, and such systems are intended to fall within the scope of the claims appended hereto.

A light source 1090 (e.g., a laser) provides light to the one or more target light sources 1020 via the dual damascene etch monitoring system 1070. Preferably, the light source 1090 is a frequency-stabilized laser, however, it will be appreciated that any laser or other light source (e.g., laser diode or helium neon (HeNe) gas laser) suitable for carrying out the present invention may be employed. One or more light detecting components 1025 (e.g., photo detector, photo diodes) collect light reflecting from the one or more gratings 1015 and/or the one or more features being etched. The dual damascene etch monitoring system 1070 may also process the measured light data into a data form compatible with or understandable to the processor 1040.

The processor 1040 is operatively coupled to the dual damascene etch monitoring system 1070 and receives the measured etching parameter data from the dual damascene etch monitoring system 1070. The processor 1040 records the acceptability of etching measurements associated with the respective portions of the wafer 1010 by examining measured etch results and comparing such measured etch result values to stored acceptable and unacceptable etch result values. The etch result values may be associated with one or more signatures stored, for example, in a memory 1050. In determining the acceptability and/or progress of an on-going and/or recently completed etch process, the processor 1040 may also determine to what extent, if any, adjustments to the etching components 1030 are desired. Upon making the determination, the processor 1040 may provide real-time feedback control to the etch process (e.g., maintain, increase, stop etching). In one example of the present invention, the processor 1040 transmits this information to the etch component driving system 1060, which then makes one or more adjustments to the etching components 1030 until desired end points for the dual damascene process have been achieved.

As described above, the processor 1040 is also coupled to the etching component driving system 1060 that directs and controls the one or more etching components 1030. The etching component driving system 1060 is controlled, at least in part, by the processor 1040 to selectively vary the operation of the respective etching components 1030. Each respective portion of the wafer 1010 is associated with a corresponding etching component 1030. The processor 1040 monitors the etching of one or more features and/or one or more gratings 1015, and selectively regulates the etching of each portion via the corresponding etching components 1030. The transmission and relay of information between the dual damascene etch monitoring system 1070, the processor 1040, the etch component driving system 1060 and the etch components 1030 facilitates generating effective real time feed back information that in turn facilitates improving IC quality by more accurately controlling the etch process.

The processor 1040, or central processing unit, may be any of a plurality of commercially available processors. The processor 1040 is programmed to monitor, control and operate the various components within the system 1000 in order to carry out the various functions described herein. The manner in which the processor 1040 is programmed to carry out the functions relating to the present invention will be apparent to those having ordinary skill in the art based on the description provided herein.

A memory 1050, which is operatively coupled to the processor 1040, is also included in the system 1000 and serves to store, among other things, program code executed by the processor 1040 for carrying out operating functions of the system 1000 as described herein. For example, the memory 1050 can hold patterns to which observed data can be compared. The memory 1050 also serves as a storage medium for temporarily storing etching parameter data such as etching progress values, etching progress tables, component coordinate tables, grating sizes, grating shapes, scatterometry information, etch measurements (e.g., CDs, depth, profile info) and other data that may be employed in carrying out the present invention.

A power supply 1080 provides operating power to the system 1000. Any suitable power supply (e.g., battery, line power) may be employed to carry out the present invention.

Figure 11:
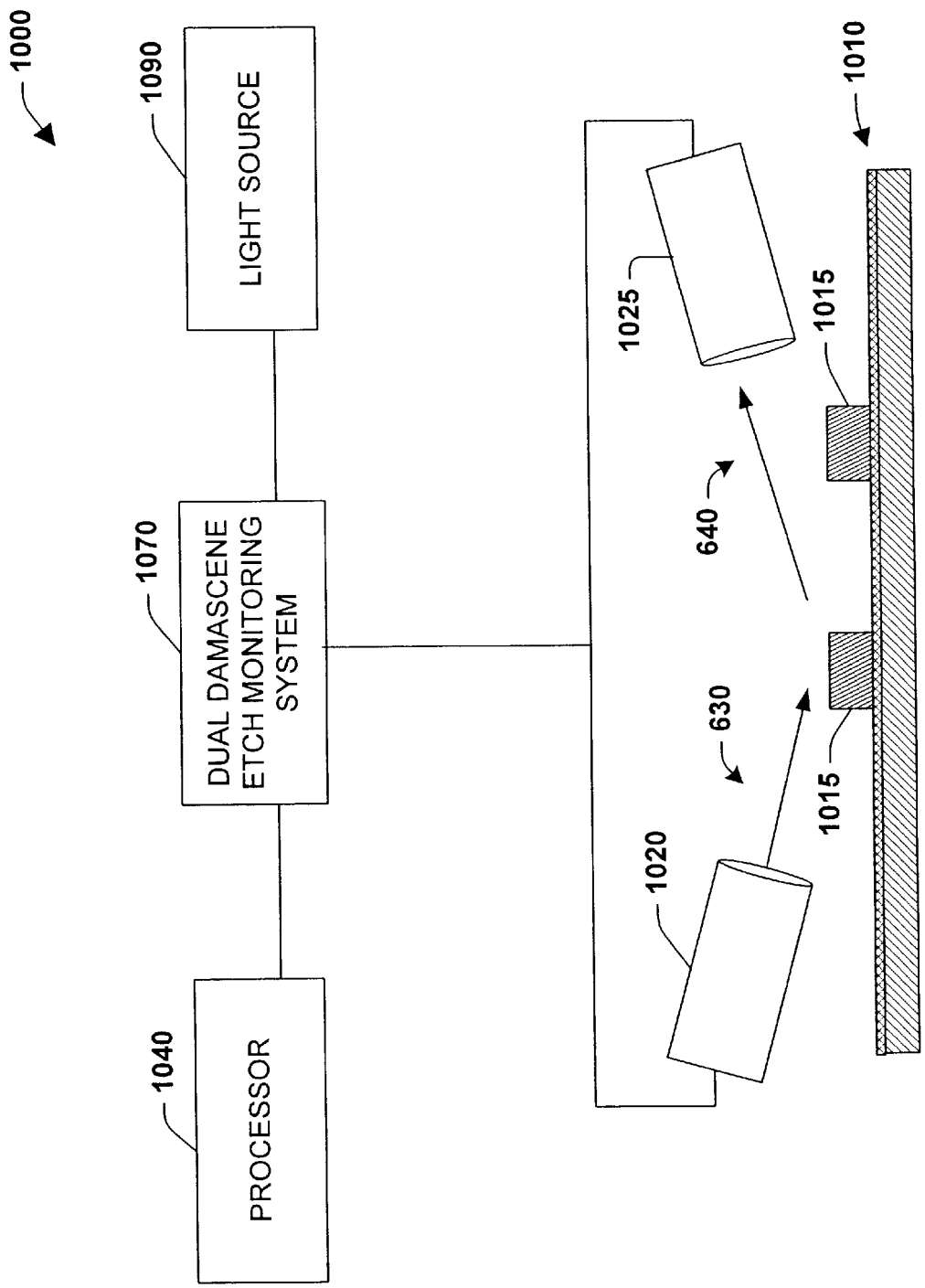
FIG. 11 is a partial schematic block diagram of the system of FIG. 10 being employed in connection with monitoring and/or controlling a dual damascene process in accordance with an aspect of present invention.

Turning now to FIG. 11, one aspect of the present invention is shown. FIG. 11 illustrates the system 1000 being employed to measure the etching of a particular portion of the wafer 1010. The target light source 1020 directs a light 630 incident to the surface of the wafer 1010. The angle of a reflected light 640, reflected from the surface of the wafer 1010, will vary in accordance with the evolving dimensions of the gratings 1015, and/or with the evolving dimensions of one or more features being etched in the wafer 1010. Thus, by comparing the evolving dimensions of the one or more features and/or gratings 1015 to desired dimensions (e.g., desired depth, geometry), etch end points can be calculated for dual damascene processes. The one or more light detecting components 1025 collect the reflected light 640 and transmit the collected light, and/or data associated with the collected light, to the dual damascene etch monitoring system 1070. The dual damascene etch monitoring system 1070 collects the reflected light 640, and/or related data, in accordance with scatterometry techniques. The dual damascene etch monitoring system 1070 then provides the processor 1040 with the data corresponding to the etching characteristics associated with the wafer 1010. The data may include, for example, information relating to the dimensions of etched areas relative to, or independent of, dimensions of unetched areas, and/or surface characteristics as well as other measurements relating to the etch process. In one example of the present invention, such relationships may be employed in linear and/or non-linear machine learning techniques to adapt etch processes characterized by the present invention.

The dual damascene etch monitoring system 1070 may provide direct, real-time measurements to the processor 1040, as opposed to measurements taken according to predetermined system schedules and measurements taken post-fabrication as is customary in conventional systems. Providing direct, real-time feedback to the processor 1040 facilitates selective adaptation of etch processes and improved etching precision over conventional methods and/or apparatus.

Turning now to FIGS. 12–14, another aspect of the present invention is shown. In addition to the methods described above, a wafer 1210 may be logically partitioned into grid blocks to facilitate identifying positions or locations associated with monitoring the etch process. Obtaining such positions or locations may facilitate determining to what extent, if any, etch process parameter adjustments are necessary and whether desired dimensions (e.g., depth, diameter) have been achieved to facilitate controlling the etch process. Obtaining such information may also assist in determining problem areas associated with etch processes.

FIG. 12 illustrates a perspective view of a chuck 1230 supporting a wafer 1210, whereupon one or more features and/or gratings may be formed. The wafer 1210 may be divided into a grid pattern as shown in FIG. 13. Each grid block (XY) of the grid pattern corresponds to a particular portion of the wafer 1210, and each grid block is associated with one or more features, gratings and/or one or more portions of one or more gratings. The grid blocks are individually monitored for etch results. It is to be appreciated that the size and/or shape of gratings can be manipulated to facilitate analyzing different etch results. For example, for a particular layer in an integrated circuit, a CD relating to the depth of a trench may be important. Thus, the gratings can be patterned to optimize analyzing depth.

In FIG. 13, one or more gratings in the respective portions of the wafer 1210 ($X_1Y_1 \ldots X_{12}, Y_{12}$) are monitored for CDs produced during the etch process using reflected light, the dual damascene etch monitoring system 1070 (FIG. 10) and the processor 1040 (FIG. 10). Exemplary CD measurements produced during etching for each grating are shown. As can be seen, the CD measurement at coordinate $X_7Y_6$ is substantially higher than the CD measurement of the other portions XY. It is to be appreciated that the wafer 1210 may be mapped into any suitable number of grid blocks, and any suitable number of gratings may formed on the wafer 1210. Although the present invention is described with respect to one etching component 1030 corresponding to one grid block XY, it is to be appreciated that any suitable number of etching components 1030 corresponding to any suitable number of wafer portions/grid blocks may be employed.

FIG. 14 is a representative table of CD measurements taken for the various grid blocks that have been correlated with acceptable CD values for the portions of the wafer 1210 mapped by the respective grid blocks. As can be seen, all the grid blocks, except grid block $X_7Y_6$, have CD measurements corresponding to an acceptable CD table value ($T_A$) (e.g., are within an expected range of etching measurements), while grid block $X_7Y_6$ has an undesired CD table value ($T_U$). Thus, the processor 1040 has determined that an undesirable etching result exists at the portion of the wafer 1210 mapped by grid block $X_7Y_6$. Accordingly, the processor 1040 may make one or more adaptations for at least an etching component $1030_{7,6}$, which corresponds to the portion of the wafer 1210 mapped at grid block $X_7Y_6$, to attempt to produce an acceptable CD.

Figure 15:
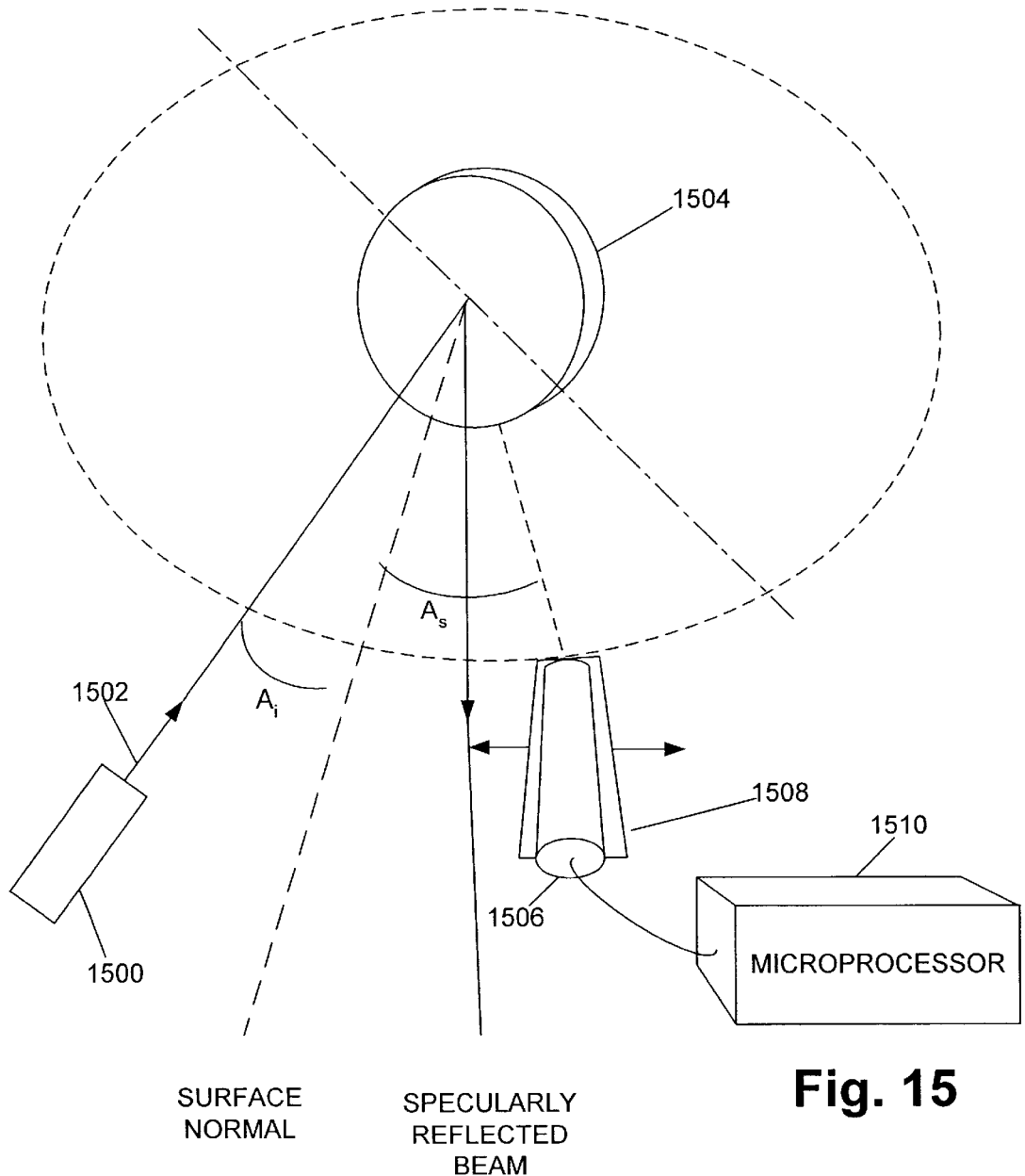
FIG. 15 illustrates an exemplary scatterometry system collecting reflected light.

FIG. 15 illustrates an exemplary scatterometry system collecting reflected light. Light from a laser 1500 is brought to focus in any suitable well-known manner to form a beam 1502. A sample, such as a wafer 1504, is placed in the path of the beam 1502 and a photo detector or photo multiplier 1506 of any suitable well-known construction. Different detector methods may be employed to determine the scattered power. To obtain a grating pitch, the photo detector or photo multiplier 1506 may be mounted on a rotation stage 1508 of any suitable well-known design. A microprocessor 1510, of any suitable well-known design, may be used to process detector readouts, including, but not limited to, angular locations of different diffracted orders leading to diffraction grating pitches being calculated. Thus, light reflected from the sample 1504 may be accurately measured.

Figure 16:
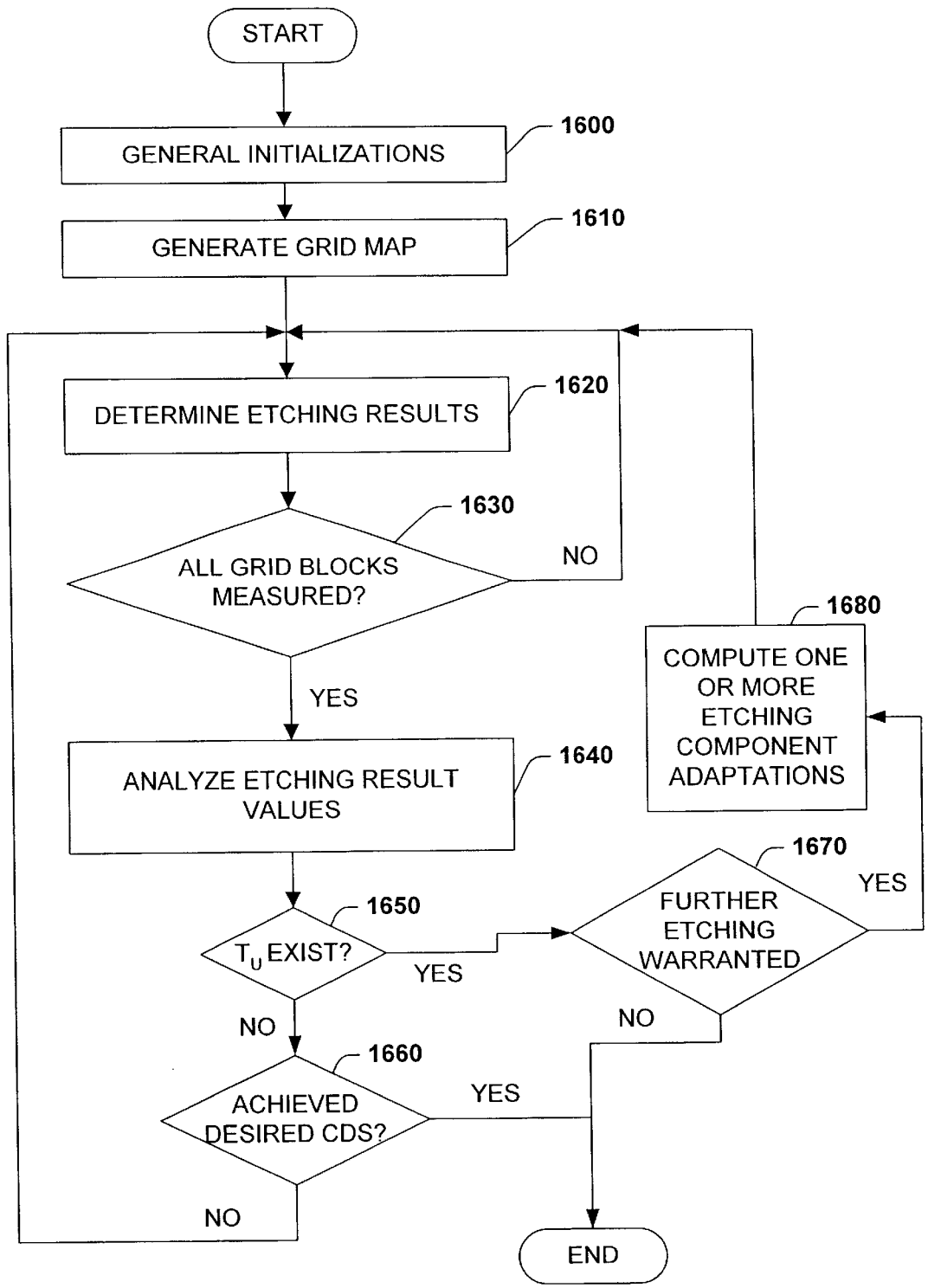
FIG. 16 is a flow diagram illustrating one specific methodology for carrying out the present invention.

In view of the exemplary systems shown and described above, methodologies that may be implemented in accordance with the present invention will be better appreciated with reference to the flow diagram of FIG. 16. While for purposes of simplicity of explanation, the methodology of FIG. 16 is shown and described as a series of blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement a methodology in accordance with the present invention.

FIG. 16 is a flow diagram illustrating one particular methodology for carrying out the present invention. At 1600, general initializations are performed. Such initializations can include, but are not limited to, establishing pointers, allocating memory, setting variables and establishing communication channels. At 1610, a grid map of a plurality of grid blocks "XY" is created. At 1620, etching results are measured from various wafer portions mapped by the respective grid blocks XY. For example, the depth of one or more trenches and/or vias may be measured. At 1630, a determination is made concerning whether all grid block measurements have been taken. If the determination at 1630 is NO, then processing returns to 1620. If the determination at 1630 is YES, then at 1640, determined etching result values are analyzed and compared against stored etching result values for the respective portions of a wafer. In an alternative example of the present invention, the determination at 1630 may concern whether a sufficient number of grid blocks have been measured to facilitate valid analysis.

At 1650, a determination is made concerning whether etching values are unacceptable. If etching values are acceptable, then processing continues at 1660 where a determination is made concerning whether desired CDs have been achieved. If desired CDs have been achieved, then processing can conclude. Otherwise, processing continues at 1620. Thus, precise control of the end point of an etch process associated with a dual damascene process can be obtained, mitigating problems associated with timed etch steps and etch-stop layers employed in conventional systems.

If unacceptable values are found at 1650, processing proceeds to 1670 where a determination is made concerning whether further etching is warranted. By way of illustration, the unacceptable values may indicate that portions of the wafer and/or the entire wafer being processed have been damaged to such an extent that further etching is unwarranted. By way of further illustration, analysis of the unacceptable dimensions may indicate that an adaptation to the etch process is appropriate (e.g., change angle of etch). At 1680, one or more adaptations to the etching components may be computed. The present iteration is then ended and the process returns to 1620 to perform another iteration.

Turning now to FIGS. 17–22, the concept of scatterometry and how it is employed in the present invention is discussed. Scatterometry is a technique for extracting information about a surface upon which an incident light has been directed. Scatterometry is a metrology that relates the geometry of a sample to its scattering effects. Scatterometry is based on the reconstruction of the grating profile from its optical diffraction responses. Information concerning properties including, but not limited to, dishing, erosion, profile, thickness of thin films and critical dimensions of features present on the surface can be extracted. The information can be extracted by comparing the phase and/or intensity of the light directed onto the surface with phase and/or intensity signals of a complex reflected and/or diffracted light resulting from the incident light reflecting from and/or diffracting through the surface upon which the incident light was directed. The intensity and/or the phase of the reflected and/or diffracted light will change based on properties of the surface upon which the light is directed. Such properties include, but are not limited to, the chemical properties of the surface, the planarity of the surface, features on the surface, voids in the surface, and the number and/or type of layers beneath the surface. In the present invention, the intensity and/or phase of the reflected and/or diffracted light will be examined as it relates to critical dimensions desired on the wafer being etched.

Different combinations of the above-mentioned properties will have different effects on the phase and/or intensity of the incident light resulting in substantially unique intensity/phase signatures in the complex reflected and/or diffracted light. Thus, by examining a signal (signature or stored value) library of intensity/phase signatures, a determination can be made concerning the properties of the surface. Such substantially unique phase/intensity signatures are produced by light reflected from and/or refracted by different surfaces due, at least in part, to the complex index of refraction of the surface onto which the light is directed. The complex index of refraction (N) can be computed by examining the index of refraction (n) of the surface and an extinction coefficient (k). One such computation of the complex index of refraction can be described by the equation:

$$N = n - jk,$$

where j is an imaginary number.

The signal (signature) library can be constructed from observed intensity/phase signatures and/or signatures generated by modeling and simulation. By way of illustration, when exposed to a first incident light of known intensity, wavelength and phase, a first feature on a wafer can generate a first phase/intensity signature. Similarly, when exposed to the first incident light of known intensity, wavelength and phase, a second feature on a wafer can generate a second phase/intensity signature. For example, a line of a first width may generate a first signature while a line of a second width may generate a second signature. Observed signatures can be combined with simulated and modeled signatures to form the signal (signature) library. Simulation and modeling can be employed to produce signatures against which measured phase/intensity signatures can be matched. In one exemplary aspect of the present invention, simulation, modeling and observed signatures are stored in a signal (signature) library containing over three hundred thousand phase/intensity signatures. Thus, when the phase/intensity signals are received from scatterometry detecting components, the phase/intensity signals can be pattern matched, for example, to the library of signals to determine whether the signals correspond to a stored signature.

Figure 17:
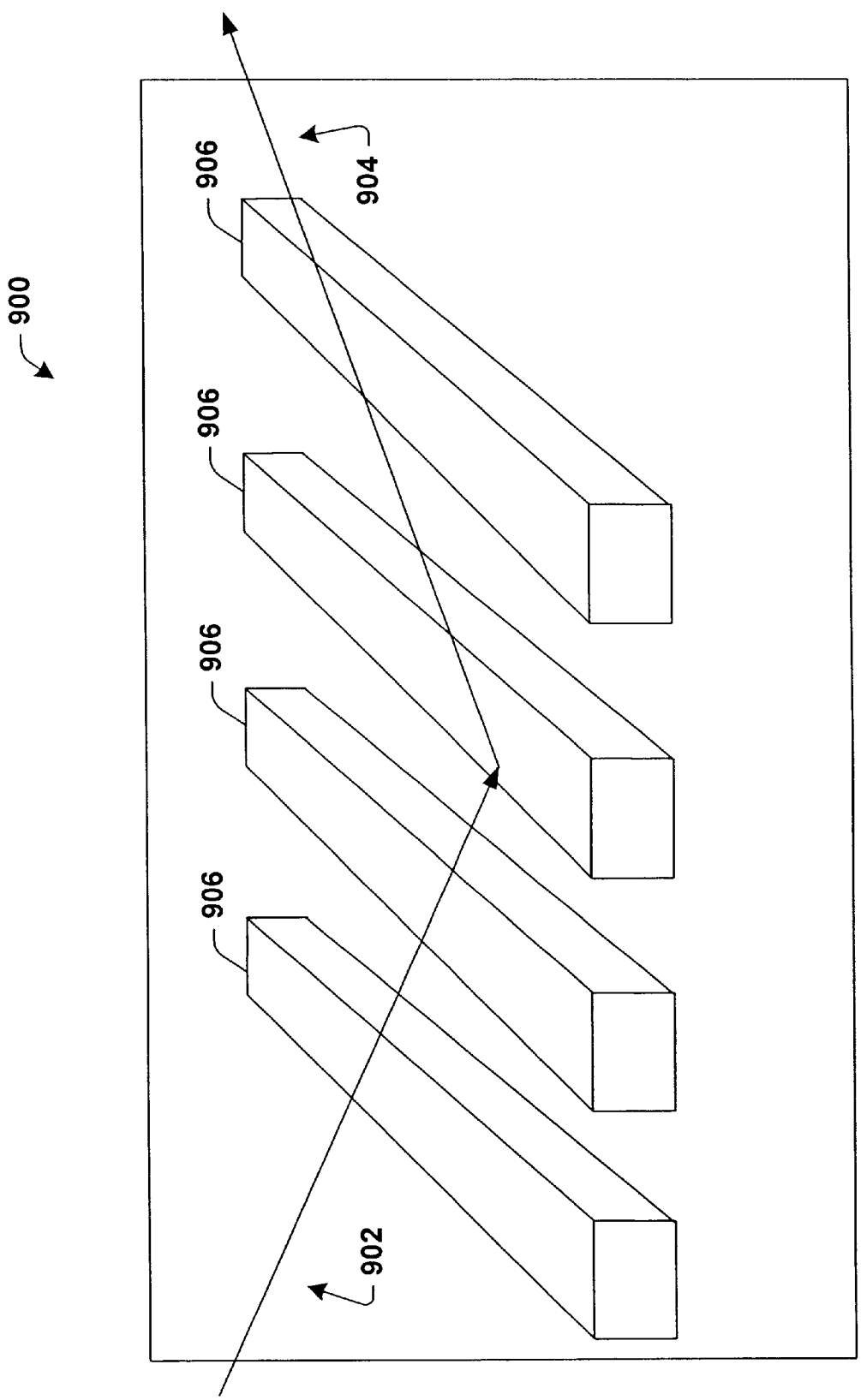
FIG. 17 is a simplified perspective view of an incident light reflecting off a surface, in accordance with an aspect of the present invention.

To illustrate the principles described above, reference is now made to FIGS. 17 through 22. Referring initially to FIG. 17, an incident light 902 is directed at a surface 900, upon which one or more features 906 may exist. The incident light 902 is reflected as reflected light 904. The properties of the surface 900, including but not limited to, thickness, uniformity, planarity, chemical composition and the presence of features, can affect the reflected light 904. The features 906 are raised upon the surface 900. The phase and intensity of the reflected light 904 can be measured and plotted, as shown, for example, in FIG. 22. The phase 960 of the reflected light 904 can be plotted, as can the intensity 962 of the reflected light 904. Such plots can be employed to compare measured signals with signatures stored in a signature library using techniques like pattern matching, for example.

Figure 18:
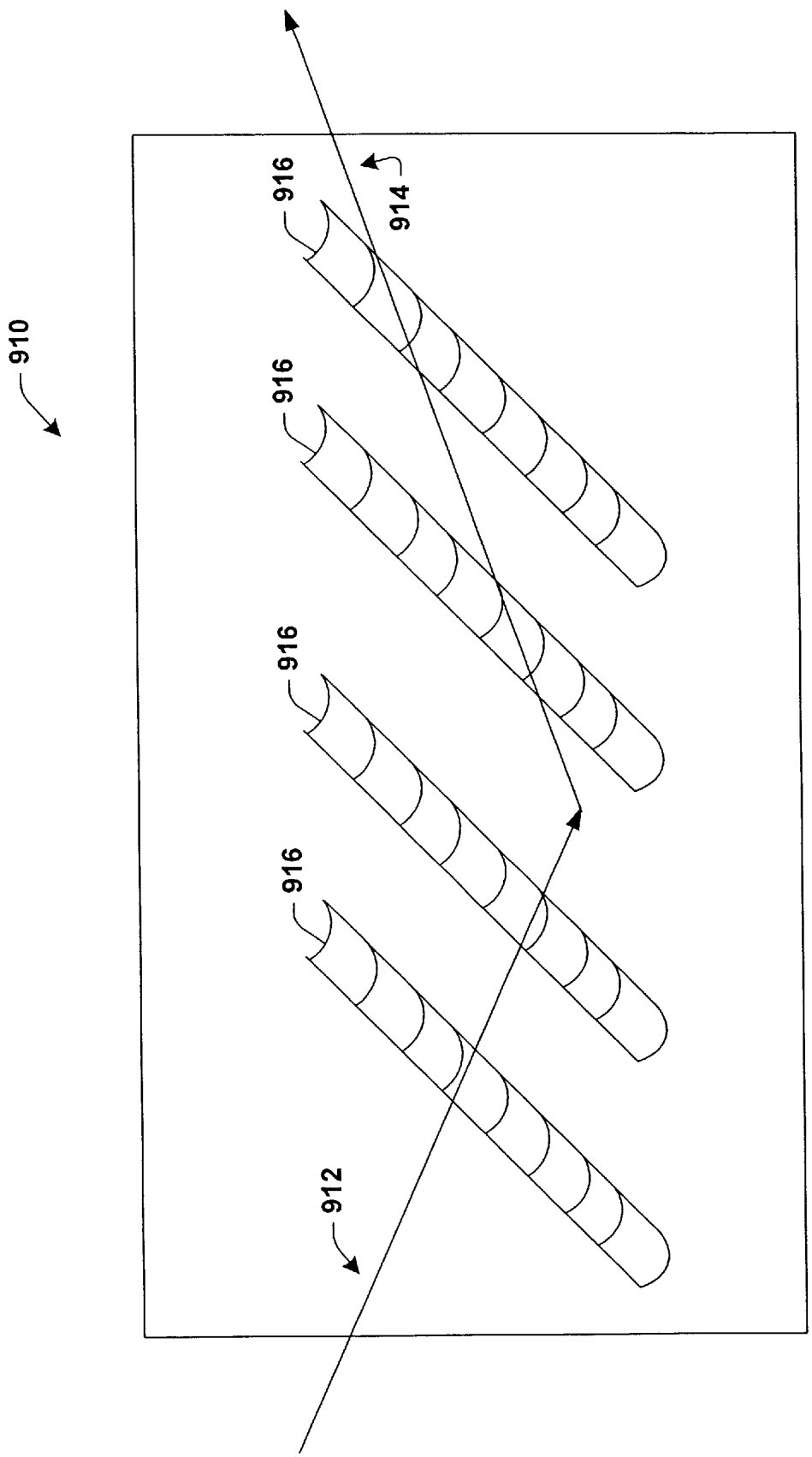
FIG. 18 is a simplified perspective view of an incident light reflecting off a surface, in accordance with an aspect of the present invention.

Referring now to FIG. 18, an incident light 912 is directed onto a surface 910 upon which one or more depressions 916 appear. The incident light 912 is reflected as reflected light 914. Like the one or more features 906 (FIG. 17) may affect an incident beam, so too may the one or more depressions 916 affect an incident beam. Thus, it is to be appreciated that scatterometry can be employed to measure features appearing on a surface, features appearing in a surface, and properties of a surface itself, regardless of features.

Figure 19:
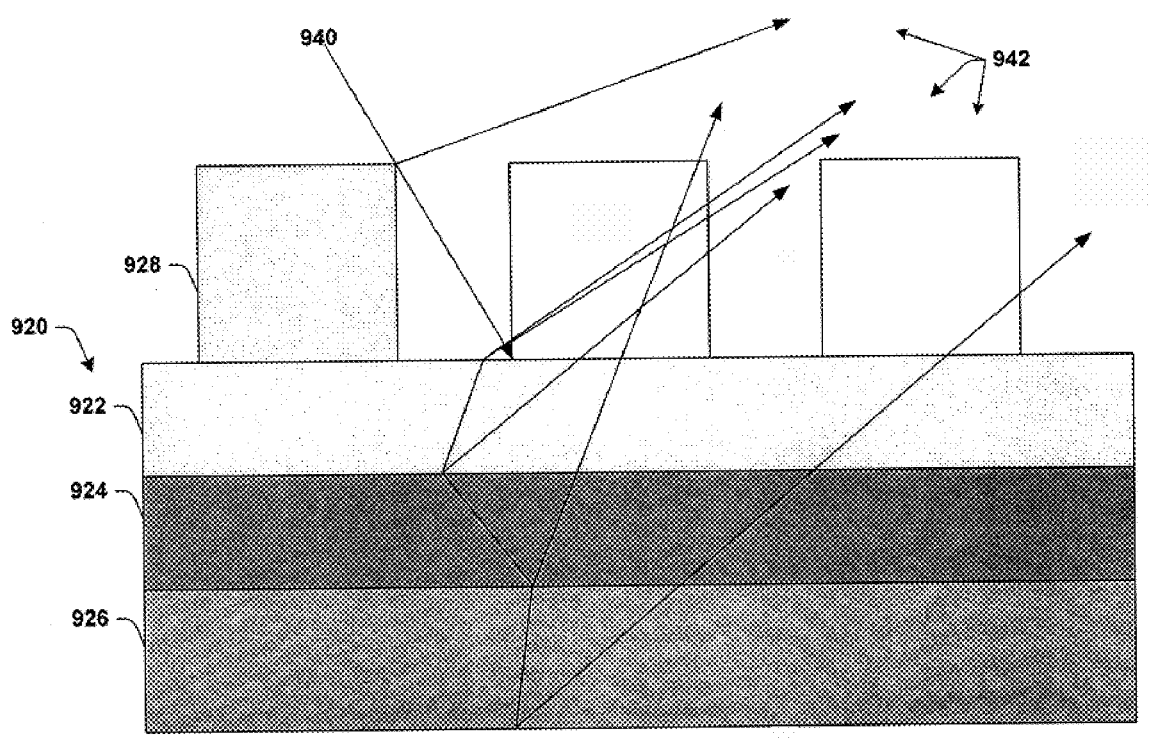
FIG. 19 illustrates a complex reflected and refracted light produced when an incident light is directed onto a surface, in accordance with an aspect of the present invention.

Turning now to FIG. 19, complex reflections and refractions of an incident light 940 are illustrated. The reflection and refraction of the incident light 940 can be affected by factors including, but not limited to, the presence of one or more features 928, and the composition of the substrate 920 upon which the features 928 reside. For example, properties of the substrate 920 including, but not limited to the thickness of a layer 922, the chemical properties of the layer 922, the opacity and/or reflectivity of the layer 922, the thickness of a layer 924, the chemical properties of the layer 924, the opacity and/or reflectivity of the layer 924, the thickness of a layer 926, the chemical properties of the layer 926, and the opacity and/or reflectivity of the layer 926 can affect the reflection and/or refraction of the incident light 940. Thus, a complex reflected and/or refracted light 942 may result from the incident light 940 interacting with the features 928, and/or the layers 922, 924 and 926. Although three layers 922, 924 and 926 are illustrated in FIG. 19, it is to be appreciated that a substrate can be formed of a greater or lesser number of such layers.

Figure 20:
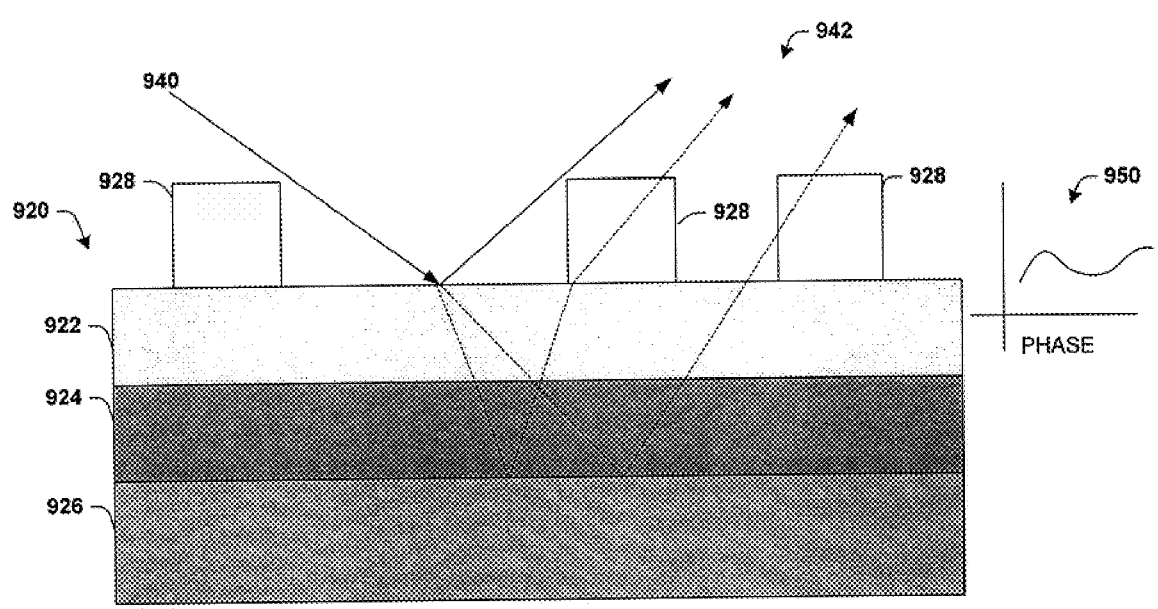
FIG. 20 illustrates a complex reflected and refracted light produced when an incident light is directed onto a surface, in accordance with an aspect of the present invention.
Figure 21:
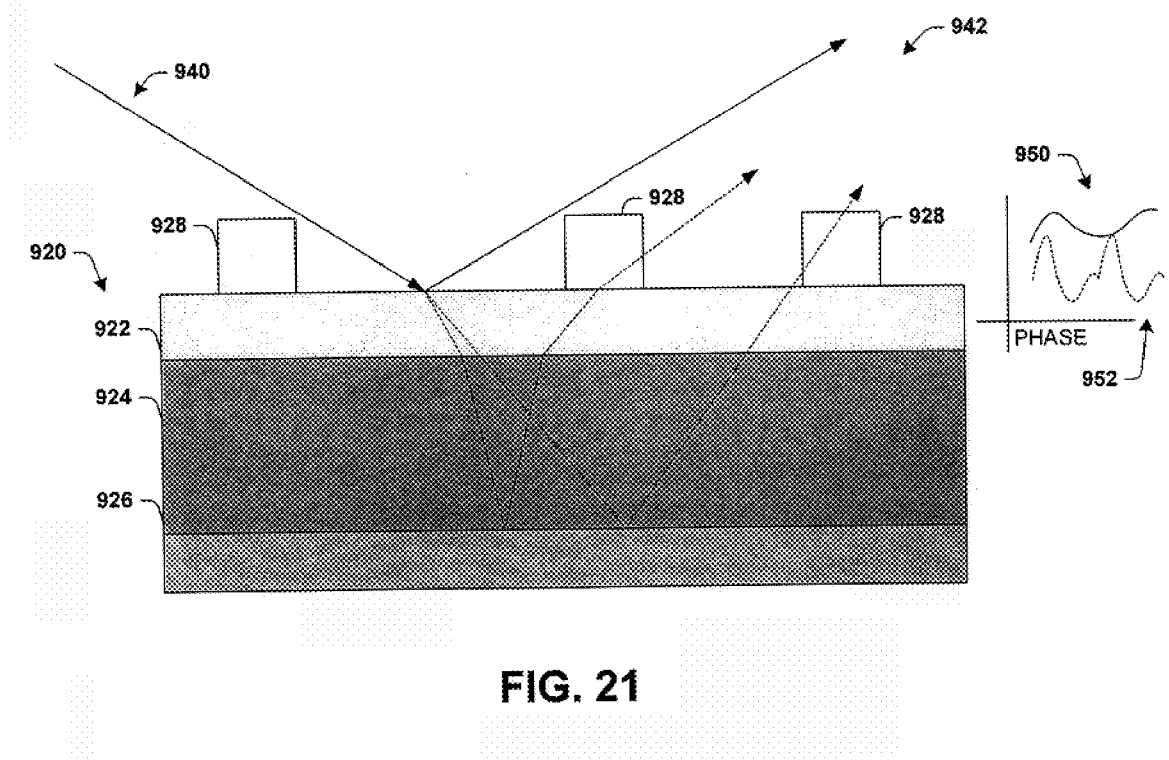
FIG. 21 illustrates a complex reflected and refracted light produced when an incident light is directed onto a surface, in accordance with an aspect of the present invention.
Figure 22:
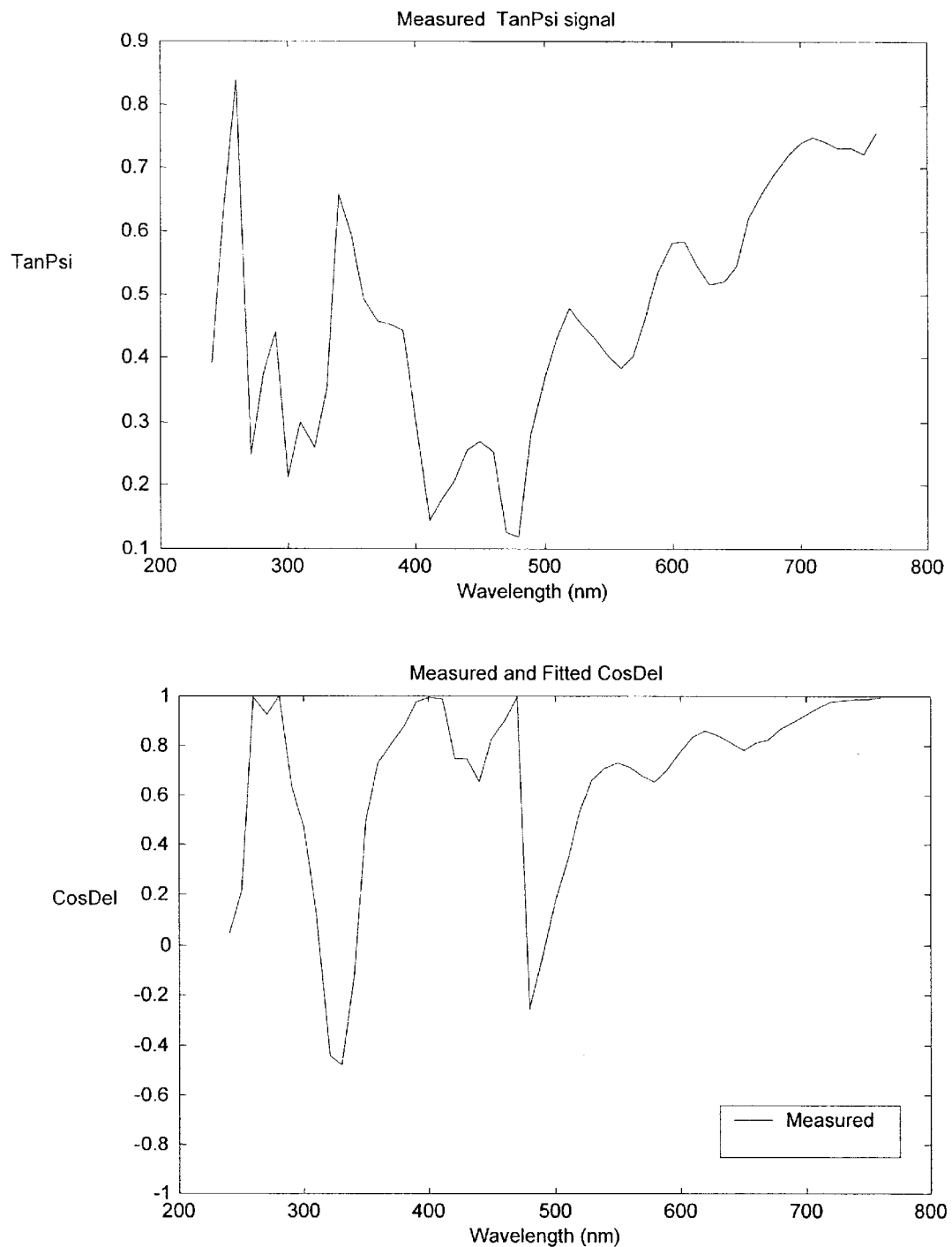
FIG. 22 illustrates phase and intensity signals recorded from a complex reflected and refracted light produced when an incident light is directed onto a surface, in accordance with an aspect of the present invention.

Turning now to FIG. 20, one of the properties from FIG. 19 is illustrated further. The substrate 920 can be formed of one or more layers 922, 924 and 926. The phase 950 of the reflected and/or refracted light 942 can depend, at least in part, on the thickness of a layer, for example, the layer 924. Thus, in FIG. 21, the phase 952 of the reflected light 942 differs from the phase 950 due, at least in part, to the different thickness of the layer 924 in FIG. 21.

Thus, scatterometry is a technique that can be employed to extract information about a surface upon which an incident light has been directed. The information can be extracted by analyzing phase and/or intensity signals of a complex reflected and/or diffracted light. The intensity and/or the phase of the reflected and/or diffracted light will change based on properties of the surface upon which the light is directed, resulting in substantially unique signatures that can be analyzed to determine one or more properties of the surface upon which the incident light was directed. Using scatterometry in the present invention facilitates a relatively non-invasive approach to controlling an etch process by identifying when desired CDs (e.g., depth, diameter, geometry) have been achieved.

Described above are preferred embodiments of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

Turning now to FIGS. 23 through 29, an example of the application and benefits of scatterometry as applied to a dual damascene process is provided. One of the advantages of present invention, removal of an etch-stop layer is particularly noted. It is to be appreciated that removing the etch-stop layer is not the only advantage of the present invention, and that other advantages (e.g., more precise end point control, real time process control) are associated with the present invention.

Figure 23:
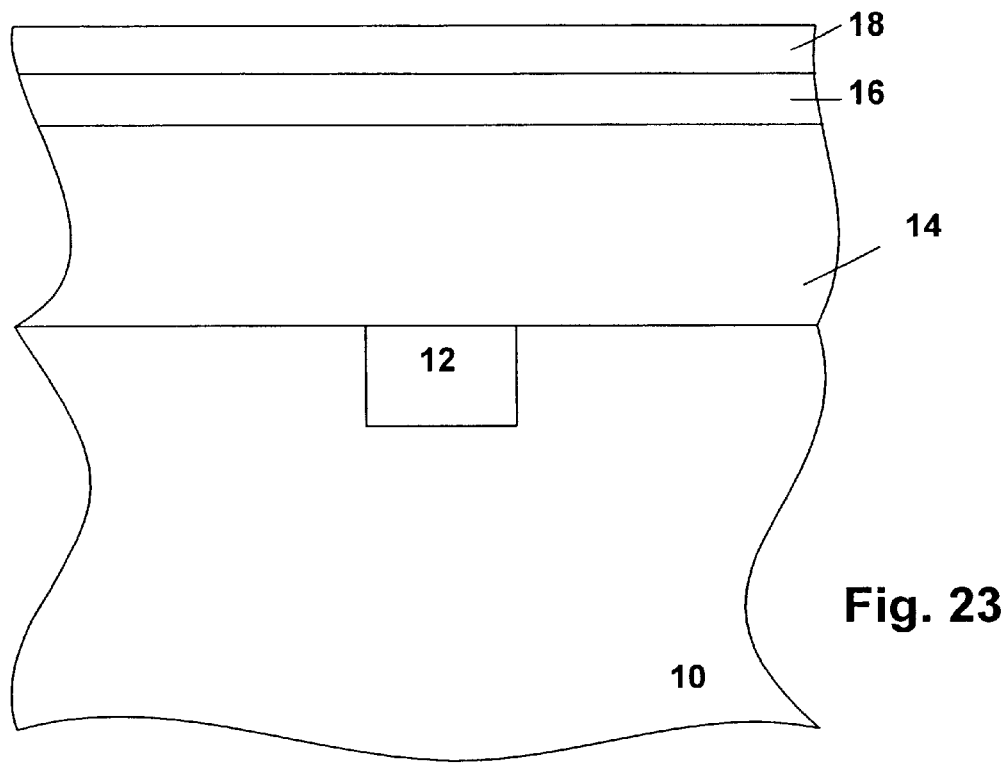
FIG. 23 illustrates a cross-sectional view of a semiconductor substrate having a low k material layer and a photoresist layer.

Referring to FIG. 23, a semiconductor substrate 10 having metal structure 12 is provided. Semiconductor substrate 10 may include any suitable semiconductor material, for example, a monocrystalline silicon substrate. Metal structure 12 may be any structure to which an electrical contact is desired, for example, a copper line. The present invention facilitates mitigating problems that the etch-stop layer is designed to prevent, and thus, the present invention facilitates performing a dual damascene process without an etch-stop layer (e.g., insulation layer 13, Prior Art FIG. 3). A low k material layer 14, such as BCB, is formed. Low k material layer 14 may be formed to any suitable thickness using any suitable technique that may depend, for instance, on the material or materials used. In the case of BCB, a spin on technique is useful.

It is to be appreciated that although FIGS. 23–29 describe a wafer with several specific layers, that the dual damascene process described in FIGS. 23–29 may be employed with other combinations of layers, and thus, the present invention is not limited to layer configurations described in connection with FIGS. 23–29.

A hard mask layer 16, such as a layer of silicon dioxide, is deposited over the low k material layer 14 using suitable techniques, such as CVD techniques. The hard mask layer 16 may alternatively include one or more of silicon nitride, silicon oxynitride, boronitride, silicon boronitride and silicon carbide. An ultra-thin photoresist layer 18 is deposited over the hard mask layer 16.

Figure 24:
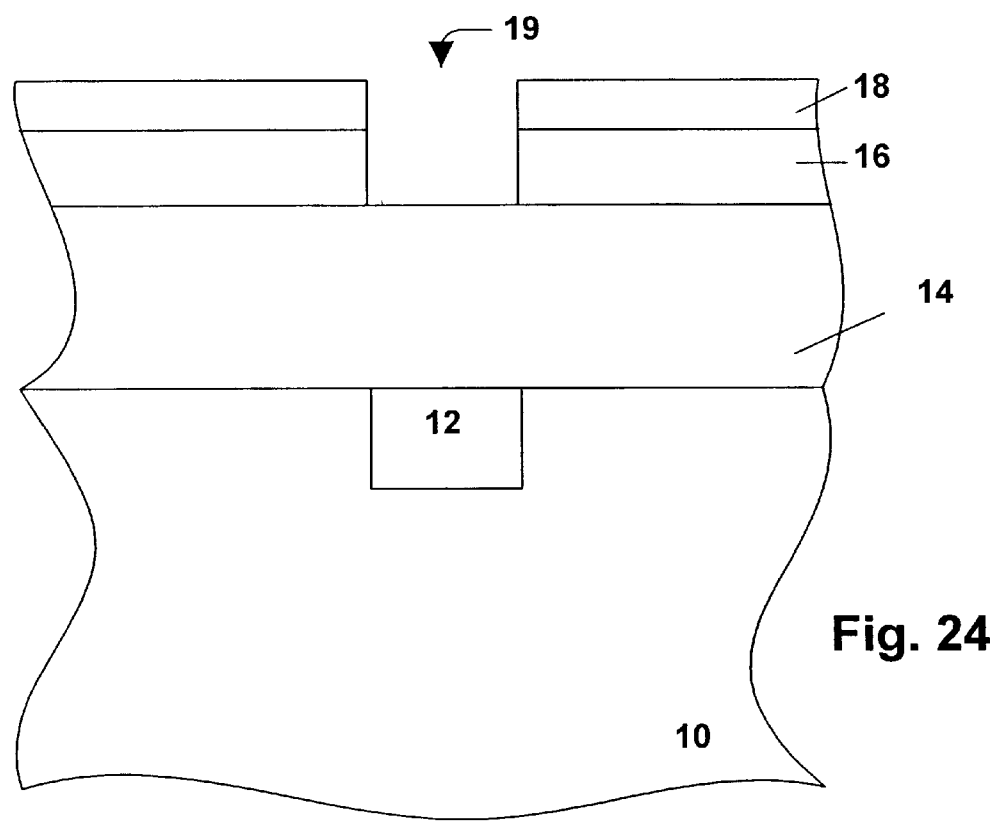
FIG. 24 illustrates a cross-sectional view of the semiconductor substrate of FIG. 23 after patterning of certain layers.

Referring to FIG. 24, the ultra-thin photoresist layer 18 and hard mask layer 16 are patterned to define a preliminary contact opening 19 over at least a portion of a device structure, active element or passive element, or the metal structure 12 in this instance. Any suitable patterning technique may be used to define the preliminary contact opening 19 in the ultra-thin photoresist layer 18 and hard mask layer 16. For example, standard photolithographic techniques may be used. In particular, the ultra-thin photoresist layer 18 is exposed to radiation and developed to provide a patterned photoresist. The patterned photoresist is formed using electromagnetic radiation having a relatively small wavelength (for example, less than 365 nm). Either the exposed or unexposed portions of the ultra-thin photoresist layer 18 are removed or developed to provide the patterned photoresist exposing a corresponding portion of the hard mask layer 16 in preliminary contact opening 19.

The exposed portions of the hard mask layer 16 are etched anisotropically to further form preliminary contact opening 16 exposing at least a portion of the low k material layer 14. The progress of the anistropic etching can be monitored by the present invention, so that the anistropic etching will proceed until desired CDs (e.g., depth, width, diameter, geometry) are achieved. Then, the present invention facilitates terminating the anistropic etch once real time information concerning desired CDs has been analyzed and thus more precise etching is achieved. The patterned ultra-thin photoresist layer 18 may then be stripped from the substrate, and the substrate may be optionally cleaned to remove residue from preliminary contact opening 19.

Preliminary contact opening 19 may be formed to have any desired cross-section, width or diameter, such as about 0.1 µm or less, including about 0.09 µm or less, about 0.075 µm or less and about 0.05 µm or less, primarily depending upon the wavelength of radiation employed. The preliminary contact openings 19 serve to define subsequently formed contact holes. Since the present invention facilitates forming the preliminary contact opening 19 more precisely, subsequently formed contact holes may also be more precisely formed, providing advantages over conventional systems.

Figure 25:
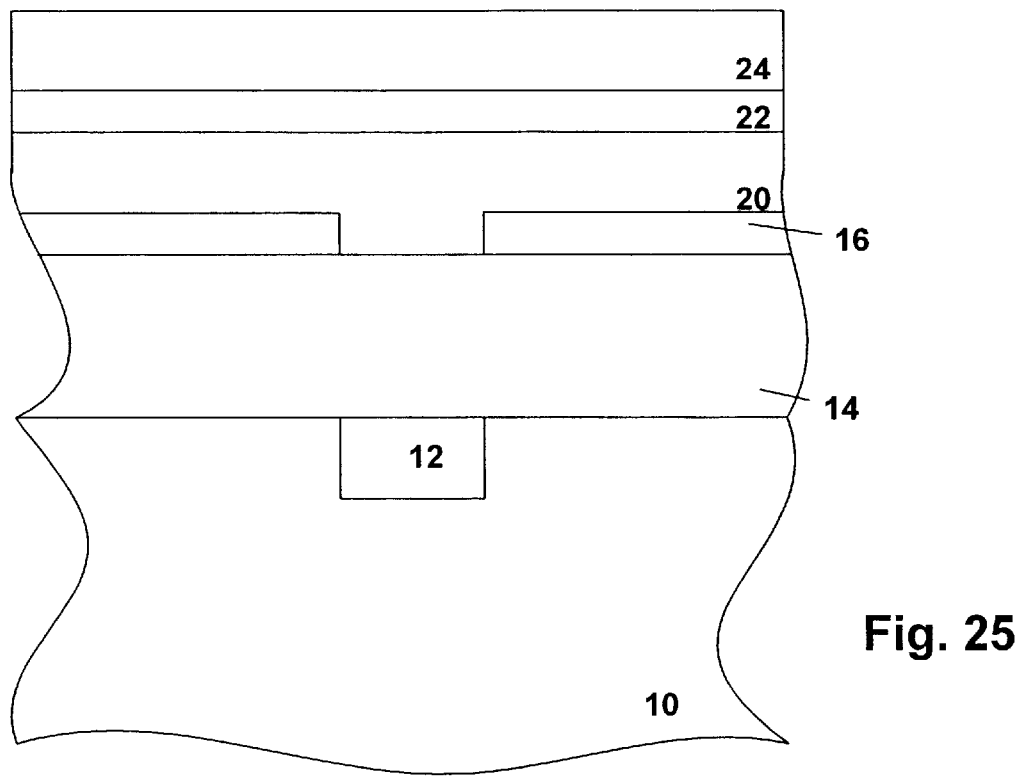
FIG. 25 illustrates a cross-sectional view of the semiconductor substrate of FIG. 24 after another low k material layer is formed.

Referring to FIG. 25, a second low k material layer 20 may be formed to any suitable thickness using any suitable technique over the substrate, including over the hard mask layer 16 and the exposed portion of the low k material layer 14 in the preliminary contact opening 19. In this embodiment, another BCB layer is formed by spin on techniques.

A second hard mask layer 22, such as a layer of silicon dioxide, is deposited over the second low k material layer 20 using suitable techniques, such as CVD techniques. The second hard mask layer 22 may alternatively include one or more of silicon nitride, silicon oxynitride, boronitride, silicon boronitride and silicon carbide.

A second ultra-thin photoresist layer 24 is deposited over the second hard mask layer 22. The second ultra-thin photoresist layer 24 and the second hard mask layer 22 subsequently serve as a trench mask for forming a trench over a plurality of contact holes.

Figure 26:
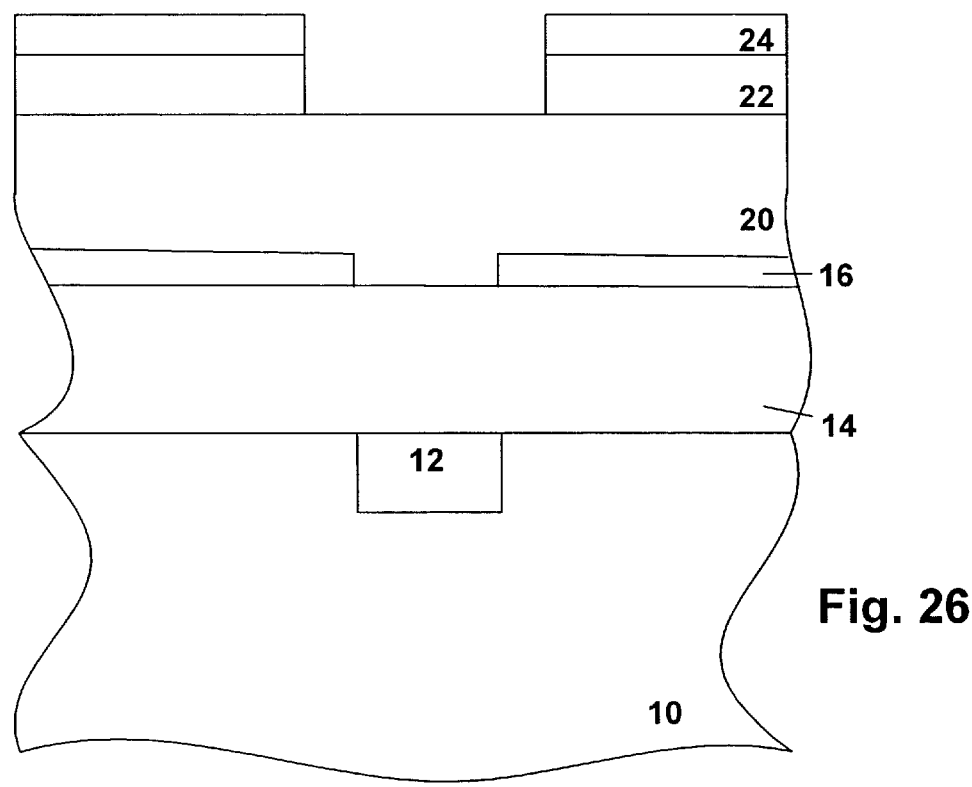
FIG. 26 illustrates a cross-sectional view of the semiconductor substrate of FIG. 25 after patterning of certain layers.

Referring to FIG. 26, the second ultra-thin photoresist layer 24 and second hard mask layer 22 are patterned to define a trench mask over at least a portion of a device structure, active element or passive element, or the metal structure 12 in this instance. Any suitable patterning technique may be used to define the trench mask in the second ultra-thin photoresist layer 24 and second hard mask layer 22. For example, standard photolithographic techniques may be used. In particular, the second ultra-thin photoresist layer 24 is exposed to radiation and developed to provide a patterned photoresist. The patterned photoresist is formed using electromagnetic radiation having a relatively small wavelength (for example, less than 365 nm). Either the exposed or unexposed portions of the second ultra-thin photoresist layer 24 are removed or developed to provide the patterned photoresist exposing a corresponding portion of the second hard mask layer 22 in the trench region.

The exposed portions of the second hard mask layer 22 are etched anisotropically to further form the trench exposing at least a portion of the second low k material layer 20. The trench may be formed to have any desired cross-section, width or diameter, such as about 0.25 $\mu$m, about 0.18 $\mu$m, about 0.15 $\mu$m, about 0.13, about 0.1 $\mu$m, about 0.075 and/or about 0.05 $\mu$m. The width of the trench may depend on the resistivity of the conductive material used for creating an interconnect within the trench. The width of the trench is typically larger than the width of previously described preliminary contact opening 19. The present invention facilitates monitoring and/or controlling the etching of the trench and thus facilitates more precisely forming the trench. Thus, the cross-section, width and/or diameter may be more precisely controlled, leading to improvements in chip quality and/or reliability.

Figure 27:
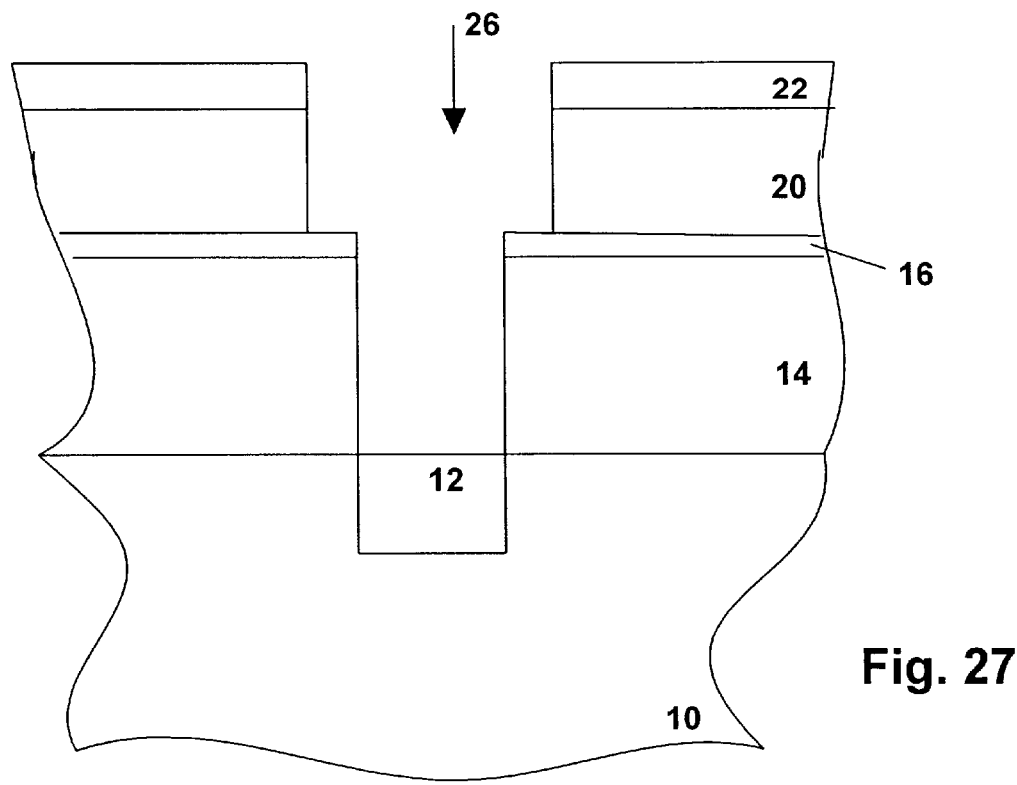
FIG. 27 illustrates a cross-sectional view of the semiconductor substrate of FIG. 26 after a portion of the low k material is removed.

Referring to FIG. 27, exposed portions of the second low k material layer 20 and low k material layer 14 are removed in any suitable manner to define an opening 26 comprised of a trench or interconnect channel over at least one contact hole formed over metal structure 12. Any suitable etch technique may be used to etch second low k material layer 20 and low k material layer 14. Conventionally, an etch-stop layer (e.g., layer 13, Prior Art FIG. 7) would be employed at this point in the dual damascene process. But the present invention facilitates etching the second low k material layer 20 and the low k material layer 14 without such an etch-stop layer. Thus, with the removal of the etch-stop layer, a simpler architecture for the integrated circuit is achieved. The second ultra-thin photoresist layer 24 may then be stripped from the substrate, and the substrate may be optionally cleaned to remove residue from the opening 26.

Figure 28:
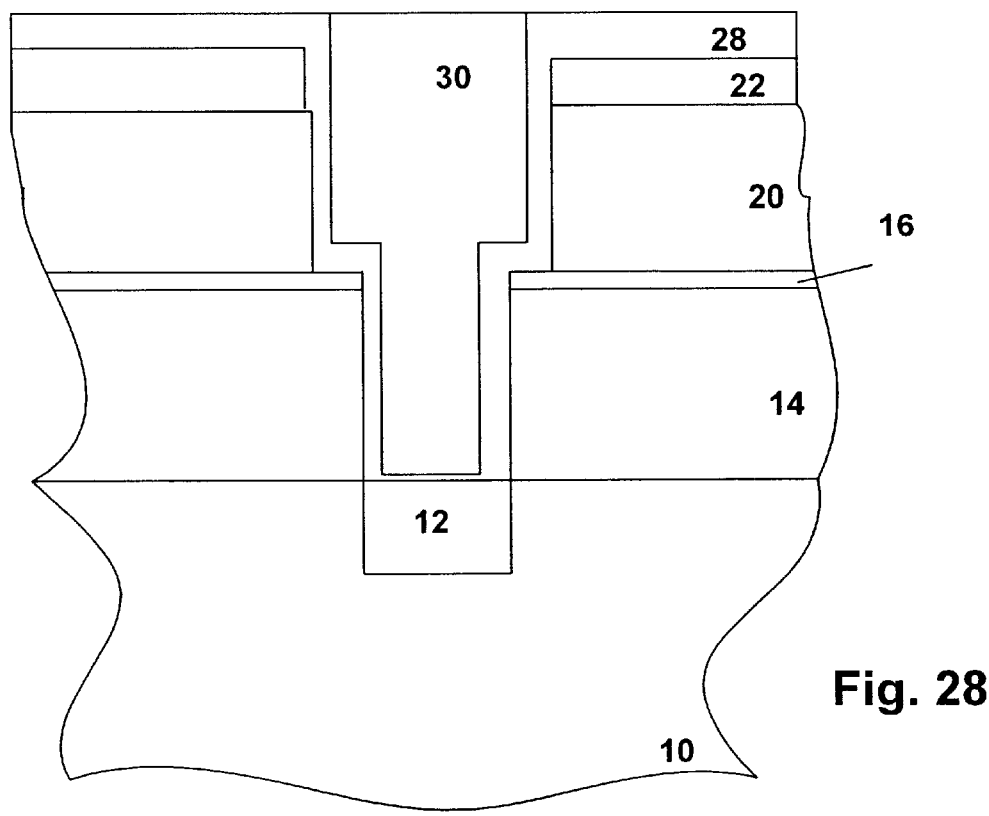
FIG. 28 illustrates a cross-sectional view of the semiconductor substrate of FIG. 27 after a barrier layer and a conductive layer are formed.
Figure 29:
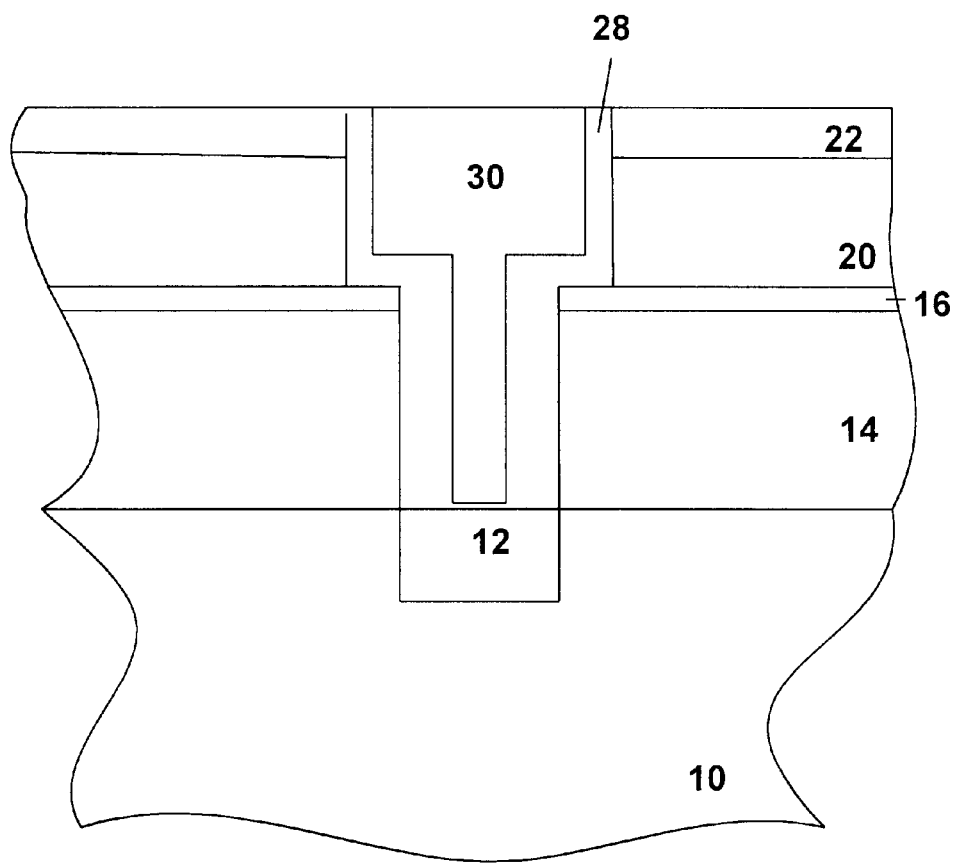
FIG. 29 illustrates a cross-sectional view of the semiconductor substrate of FIG. 28 after the substrate is planarized.

Referring to FIGS. 28 and 29, processing substantially similar to that of Prior Art FIGS. 8 and 9 is undertaken to complete the portion of the dual damascene process. Thus, through the use of scatterometry based monitoring and control of the etching in the dual damascene process illustrated in FIGS. 23–29, a simpler wafer architecture and more precise feature forming are achieved. It is to be appreciated that FIGS. 23–29 illustrate but one example dual damascene process, and that the present invention is not limited to improving the illustrated dual damascene process, but that the present invention can be employed to improve other, non-illustrated dual damascene processes.

What is claimed is:

1. A system for real-time monitoring and controlling an etch process, comprising:

a wafer that does not contain an etch stop layer;

at least one etching component operative to etch at least one portion of the wafer;

an etch component driving system operably connected to the at least one etching component, the etch component driving system adapted to drive the at least one etching component;

a system for directing light toward one or more gratings and/or features located on at least one portion of the wafer during operation of the etching component;

an etch monitoring system operable to measure one or more etching results from light reflected from the one or more gratings and/or features during operation of the etching component; and a processor operatively coupled to the etch monitoring system and the etch component driving system, wherein the processor receives an etching result data from the measuring system and analyzes the etching result data by comparing the etching result data to stored etching result data during operation of the etching component.

2. The system of claim 1, the etch monitoring system further including a scatterometry system for processing the light reflected from the one or more gratings and/or features.

3. The system of claim 2, the processor being operatively coupled to the scatterometry system, the processor analyzing data received from the scatterometry system and producing an analyzed data.

4. The system of claim 3, wherein the processor determines that a desired critical dimension has been achieved and controls one or more etching components to terminate etching.

5. The system of claim 4, wherein the etch process is at least one of an isotropic etch process and an anisotropic etch process.

6. The system of claim 4, wherein the etch process is a dry-etching process where the mechanism of etching has at least one of a physical basis, a chemical basis and a combination of physical and chemical bases.

7. The system of claim 6, wherein the dry-etching technique with a mechanism of etching as a physical basis is at least one of a glow-discharge sputtering technique and an ion-milling technique.

8. The system of claim 6, wherein the dry-etching technique with a mechanism of etching as a chemical basis is a plasma etching technique.

9. The system of claim 6, wherein the dry-etching technique with a combination of bases is at least one of a reactive ion etching (RIE) technique and an ion-enhanced etching technique.

10. The system of claim 4, the processor logically mapping the wafer into one or more grid blocks and making a determination of the acceptability of etching values in the one or more grid blocks.

11. The system of claim 10, wherein the processor determines the existence of unacceptable etching values for at least a portion of the wafer based on comparing one or more measured etching values to one or more stored etching values.

12. The system of claim 11, wherein the processor generates real time feed forward data operable to adapt one or more etch components.

13. The system of claim 12, wherein the processor employs a machine-learning system in generating the real time feed forward data.

14. A system for real-time monitoring an etch process, comprising:

means for partitioning a wafer into one or more grid blocks;

means for etching a wafer, wherein the wafer does not contain an etch stop layer;

scatterometry means for monitoring the etching in the one or more grid blocks during operation of the etching means; and means for determining the desirability of one or more etch results achieved in the one or more grid blocks during operation of the etching means.

15. The system of claim 14, further comprising means for terminating the etch process.

16. A system for real-time monitoring and controlling an etch process associated with a dual damascene process, comprising:

a wafer that does not contain an etch stop layer;

at least one etching component operative to etch a dual damascene opening comprising a trench and contact holes at least one portion of the wafer;

an etch component driving system operably connected to the at least one etching component, the etch component driving system adapted to drive the at least one etching component;

a system for directing light toward one or more gratings and/or features located on at least one portion of the wafer during operation of the etching component;

an etch monitoring system operable to measure one or more etching results from light reflected from the one or more gratings and/or features during operation of the etching component; and a processor operatively coupled to the etch monitoring system and the etch component driving system, wherein the processor receives an etching result data from the measuring system and analyzes the etching result data by comparing the etching result data to stored etching result data during operation of the etching component.

* * * * *